(12) United States Patent
Gharib et al.

(10) Patent No.: US 8,055,349 B2
(45) Date of Patent: Nov. 8, 2011

(54) SYSTEM AND METHODS FOR DETERMINING NERVE PROXIMITY, DIRECTION, AND PATHOLOGY DURING SURGERY

(75) Inventors: James Gharib, San Diego, MN (US); Norbert F. Kaula, Arvada, CO (US); Allen Farquhar, Portland, OR (US); Jeffrey J. Blewett, San Diego, CA (US); Goretti Medeiros, legal representative, Plantsville, CT (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/080,493

(22) Filed: Apr. 5, 2011

(65) Prior Publication Data
US 2011/0184308 A1    Jul. 28, 2011

Related U.S. Application Data

(60) Division of application No. 12/711,937, filed on Feb. 24, 2010, now Pat. No. 7,920,922, which is a continuation of application No. 10/754,899, filed on Jan. 9, 2004, which is a continuation of application No. PCT/US02/22247, filed on Jul. 11, 2002.

(51) Int. Cl.
*A61B 5/05* (2006.01)
(52) U.S. Cl. .......................................... 607/48; 600/554
(58) Field of Classification Search .................. 600/554; 607/48
See application file for complete search history.

(56) References Cited

U.S. PATENT DOCUMENTS

| | | | |
|---|---|---|---|
| 208,227 A | 9/1878 | Dorr | |
| 4,611,597 A | 9/1986 | Kraus | |
| 4,913,134 A | 4/1990 | Luque | |
| 5,171,279 A | 12/1992 | Mathews | |
| 5,195,541 A | 3/1993 | Obenchain | |
| 5,295,994 A | 3/1994 | Bonutti | |
| 5,331,975 A | 7/1994 | Bonutti | |
| 5,342,384 A | 8/1994 | Sugarbaker | |
| 5,378,241 A | 1/1995 | Haindl | |
| 5,395,317 A | 3/1995 | Kambin | |
| 5,450,845 A | 9/1995 | Alexgaard | |
| 5,509,893 A | 4/1996 | Pracas | |
| 5,514,153 A | 5/1996 | Bonutti | |
| 5,571,149 A | 11/1996 | Liss et al. | |
| 5,667,508 A | 9/1997 | Errico et al. | |
| 5,681,265 A | 10/1997 | Maeda et al. | |
| 5,762,629 A | 6/1998 | Kambin | |
| 5,792,044 A | 8/1998 | Foley et al. | |
| 5,817,071 A | 10/1998 | Dewindt et al. | |

(Continued)

FOREIGN PATENT DOCUMENTS
JP    11-076430    3/1999
(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Michael Kahelin
(74) *Attorney, Agent, or Firm* — Jonathan Spangler; Rory Schermerhorn; Fish & Richardson P.C.

(57) ABSTRACT

The present invention involves systems and methods for determining nerve proximity, nerve direction, and pathology relative to a surgical instrument based on an identified relationship between neuromuscular responses and the stimulation signal that caused the neuromuscular responses.

24 Claims, 15 Drawing Sheets

U.S. PATENT DOCUMENTS

| | | | |
|---|---|---|---|
| 5,935,131 | A | 8/1999 | Bonutti et al. |
| 5,938,688 | A | 8/1999 | Schiff |
| 5,944,658 | A | 8/1999 | Koros et al. |
| 5,976,146 | A | 11/1999 | Ogawa et al. |
| 6,004,312 | A | 12/1999 | Finnerman |
| 6,007,487 | A | 12/1999 | Foley et al. |
| 6,095,987 | A | 8/2000 | Shmulewitz |
| 6,146,371 | A | 11/2000 | Dewindt et al. |
| 6,152,871 | A | 11/2000 | Foley et al. |
| 6,174,311 | B1 | 1/2001 | Branch et al. |
| 6,196,969 | B1 | 3/2001 | Bester et al. |
| 6,217,509 | B1 | 4/2001 | Foley et al. |
| 6,217,527 | B1 | 4/2001 | Selmon et al. |
| 6,221,049 | B1 | 4/2001 | Selmon et al. |
| 6,231,546 | B1 | 5/2001 | Milo et al. |
| 6,270,505 | B1 | 8/2001 | Yoshida et al. |
| 6,395,007 | B1 | 5/2002 | Bhatnagar et al. |
| 6,447,484 | B1 | 9/2002 | Briscoe et al. |
| 6,468,205 | B1 | 10/2002 | Mollenauer et al. |
| 6,468,207 | B1 | 10/2002 | Fowler, Jr. |
| 6,514,217 | B1 | 2/2003 | Selmon et al. |
| 6,520,907 | B1 | 2/2003 | Foley et al. |
| 6,524,320 | B2 | 2/2003 | DiPoto |
| 6,535,759 | B1 | 3/2003 | Epstein et al. |
| 6,620,157 | B1 | 9/2003 | Dabney et al. |
| 6,641,613 | B2 | 11/2003 | Sennett |
| 6,645,194 | B2 | 11/2003 | Briscoe et al. |
| 6,679,833 | B2 | 1/2004 | Smith et al. |
| 6,810,281 | B2 | 10/2004 | Brock et al. |
| 6,916,330 | B2 | 7/2005 | Simonson |
| 6,945,933 | B2 | 9/2005 | Branch |
| 7,008,431 | B2 | 3/2006 | Simonson |
| 7,047,082 | B1 | 5/2006 | Schrom et al. |
| 7,198,598 | B2 | 4/2007 | Smith et al. |
| 7,226,451 | B2 | 6/2007 | Shluzas et al. |
| 7,276,055 | B2 | 10/2007 | Dewindt et al. |
| 7,311,719 | B2 | 12/2007 | Bonutti |
| 7,470,236 | B1 | 12/2008 | Kelleher et al. |
| 7,582,058 | B1 | 9/2009 | Miles et al. |
| 2002/0010392 | A1 | 1/2002 | Desai |
| 2002/0123780 | A1 | 9/2002 | Grill et al. |
| 2003/0139648 | A1 | 7/2003 | Foley et al. |
| 2003/0149341 | A1 | 8/2003 | Clifton |
| 2003/0225405 | A1 | 12/2003 | Weiner |
| 2004/0181231 | A1 | 9/2004 | Emstad et al. |
| 2005/0033380 | A1 | 2/2005 | Tanner et al. |
| 2005/0149035 | A1 | 7/2005 | Pimenta et al. |
| 2005/0192575 | A1 | 9/2005 | Pacheco |
| 2008/0097164 | A1 | 4/2008 | Miles et al. |
| 2008/0300465 | A1 | 12/2008 | Feigenwinter et al. |
| 2009/0124860 | A1 | 5/2009 | Miles et al. |
| 2009/0138050 | A1 | 5/2009 | Ferree |
| 2009/0192403 | A1 | 7/2009 | Gharib et al. |
| 2009/0204016 | A1 | 8/2009 | Gharib et al. |

FOREIGN PATENT DOCUMENTS

| | | |
|---|---|---|
| JP | 2001-170190 | 6/2001 |
| WO | 00/62660 | 10/2000 |
| WO | 02/054960 | 7/2002 |
| WO | 03/005887 | 1/2003 |
| WO | 03/026482 | 4/2003 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.

METRx Delivered Order Form, 1999, 13 pages.

Medtronic Sofamor Danek "METRx™ MicroDisectomy System," *Medtronic Sofamor Danek USA*, 2000, 21 pgs.

Medtronic Sofamor Danek "METRx System Surgical Technique," 2004, 22 pages.

"MetRx System MicroEndoscopic Discectomy: An Evolution in Minimally Invasive Spine Surgery," *Sofamor Danek*, 1999, 6 pages.

Smith and Foley "MetRx System MicroEndoscopic Discectomy: Surgical Technique" *Medtronic Sofamor Danek*, 2000, 24 pages.

"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.

Japanese Patent Office JP Patent Application No. 2006-528306 Office Action with English Translation, Jun. 10, 2009, 4 pages.

Plaintiffs' Preliminary Invalidity Contentions re US Patents 7207949; 7470236 and 7582058, Sep. 18, 2009, 19 pages.

Plaintiffs' Preliminary Invalidity Contentions-Appendices, Sep. 18, 2009, 191 pages.

Plaintiffs' Supplemental Preliminary Invalidity Contentions re US Patents 7207949, 7470236, and 7582058, Sep. 29, 2009, 21 pages.

Plaintiffs' Supplemental Preliminary Invalidity Contentions-Appendices, Sep. 29, 2009, 294 pages.

Axon 501(k) Notification: Epoch 2000 Neurological Workstation, Dec. 3, 1997, 464 pages.

Foley and Smith, "Microendoscopic Discectomy," *Techniques in Neurosurgery*, 1997, 3(4):301-307.

Medtronic Sofamor Danek "UNION™ / UNION-L™ Anterior & Lateral Impacted Fusion Devices: Clear choice of stabilization," *Medtronic Sofamor Danek*, 2000, 4 pages.

NuVasive Vector™ Cannulae, 2000, 1 page.

NuVasive Triad™ Tri-Columnar Spinal EndoArthrodesis™ via Minimally Invasive Guidance, 2000, 1 page.

NuVasive Triad™ Cortical Bone Allograft, 2000, 1 page.

NuVasive Vertebral Body Access System, 2000, 1 page.

Marina, "New Technology for Guided Navigation with Real Time Nerve Surveillance for Minimally Invasive Spine Discectomy & Arthrodesis," *Spineline*, 2000, p. 39.

NuVasive "INS-1 Screw Test," 2001, 10 pages.

NuVasive letter re 510k Neuro Vision JJB System, Oct. 16, 2001, 5 pages.

NuVasive letter re 510k Guided Arthroscopy System, Oct. 5, 1999, 6 pages.

NuVasive letter re 510k INS-1 Intraoperative Nerve Surveillance System, Nov. 13, 2000, 7 pages.

"NuVasiveTM Receives Clearance to Market Two Key Elem Minimally Invasive Spine Surgery System," Nov. 27, 2001, 20 pages.

Schick et al., "Microendoscopic lumbar discectomy versus open surgery: an intraoperative EMG study," *Eur Spine J*, 2002, 11: 20-26.

NuVasive letter re: 510(k) for Neurovision JJB System (Summary), Sep. 25, 2001, 28 pages.

NuVasive letter re: Special 510(k) Premarket Notification: Neurovision JJB System (Device Description), Jul. 3, 2003, 18 pages.

NuVasive letter re: Special 510(k) Premarket Notification: Neurovision JJB System (Device Description), Mar. 1, 2004, 16 pages.

NuVasive letter re: Special 510(k) Premarket Notification: Neurovision JJB System (Device Description), May 26, 2005, 17 pages.

NuVasive letter re: 510(k) Premarket Notification: Neurovision JJB System (Device Description), Jun. 24, 2005, 16 pages.

NuVasive letter re: Special 510(k) Premarket Notification: Neurovision JJB System (Device Description), Sep. 14, 2006, 17 pages.

NuVasive 510(k) Premarket Notification: Neurovision JJB System (Device Description), Aug. 20, 2007, 8 pages.

NuVasive letter re: 510(k) Premarket Notification: Guided Spinal Arthroscopy System (Device Description), Feb. 1, 1999, 40 pages.

NuVasive 510(k) Premarket Notification: Spinal System (Summary), Apr. 12, 2004, 10 pages.

NuVasive 510(k) Summary NIM Monitor, Sep. 4, 1998, 4 pages.

NuVasive correspondence re 510(k) Premarket Notification INS-1 Intraoperative Nerve Surveillance System: Section IV Device Description, pp. 12-51 (prior to Sep. 25, 2003).

Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2):93-126.

Mathews et al., "Laparoscopic Discectomy with Anterior Lumbar Interbody Fusion," *SPINE*, 1995, 20(16): 1797-1802.

Rose et al., "Persistently Electrified Pedicle Stimulation Instruments in Spinal Instrumentation: Techniques and Protocol Development," *SPINE*, 1997, 22(3): 334-343.

Medtronic Sofamor Danek "UNION™ /UNION-L™ Anterior & Lateral Impacted Fusion Devices: Surgical Technique" *Medtronic Sofamor Danek*, 2001, 20 pages.

Defendant's Disclosure of Asserted Claims and Preliminary Infringement Contentions Regarding USP 7207949; 7470236 and 7582058, Aug. 31, 2009, 21 pages.

Bergey et al., "Endoscopic Lateral Transpsoas Approach to the Lumbar Spine," *Spine*, 2004, 29(15):1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10:396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Larson, Sanford J. et al., "Surgery of the Lumbar Spine," 1999, pp. 305-319.

Medtronic Xomed Surgical Products, Inc. "NIM-Response Nerve Integrity Monitor Intraoperative EMG Monitor User's Guide, Revision B," 2000.

Pimenta, Luiz. "Initial Clinical Results of Direct Lateral, Minimally Invasive Access to the Lumbar Spine for Disc Nucleus Replacement Using a Novel Neurophysiologica Monitoring System." The 9$^{th}$ IMAST: May 2002. 1 page.

"The Lateral Endoscopic Transpsoas Retroperitoneal Approach (Letra) for Implants in the Lumbar Spine" Second Interdisciplinary Congress on Spine Care World Spine II: Aug. 2003, 2 pages.

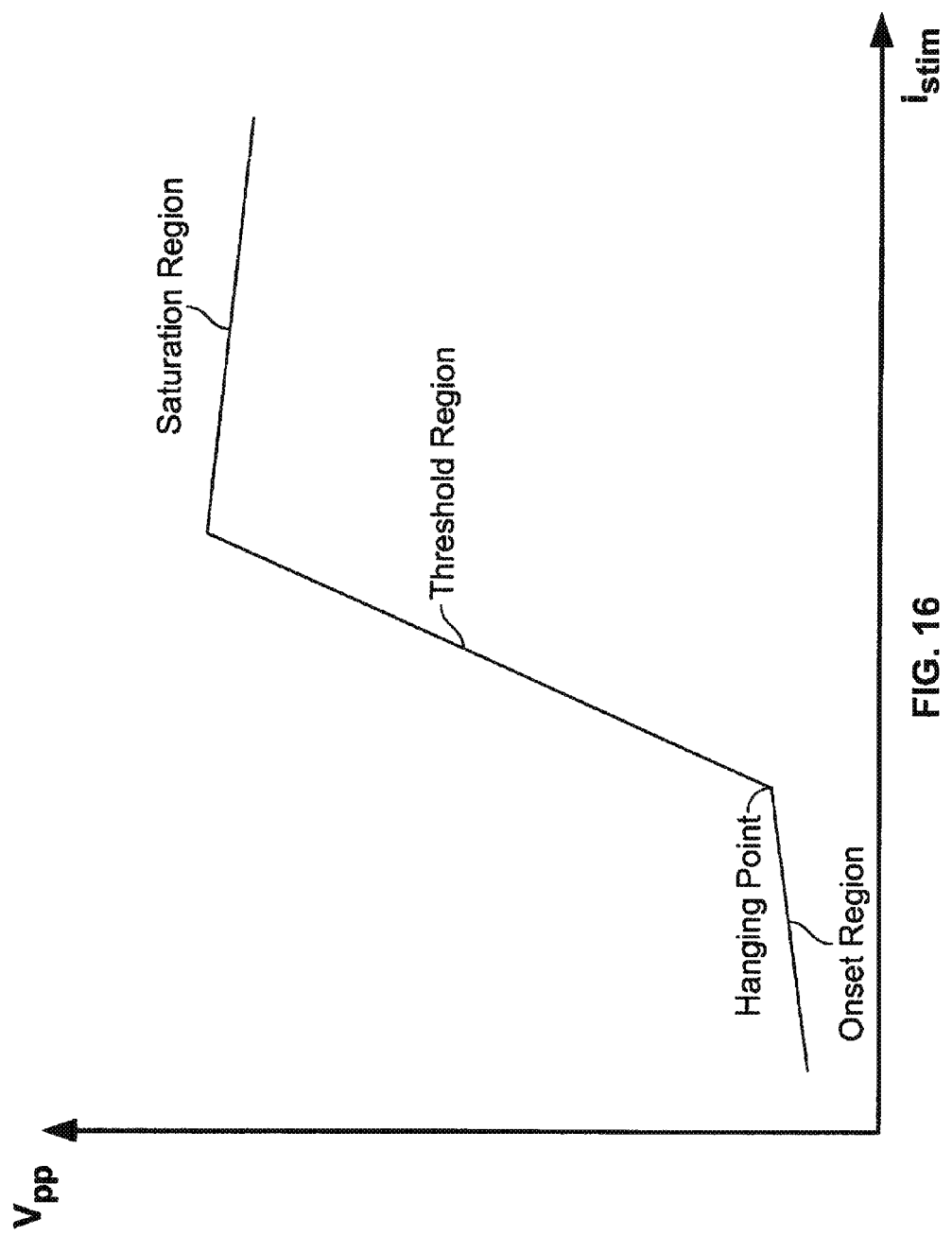

SYSTEM AND METHODS FOR DETERMINING NERVE PROXIMITY, DIRECTION, AND PATHOLOGY DURING SURGERY

CROSS-REFERENCES TO RELATED APPLICATIONS

This application is a division of U.S. patent application Ser. No. 12/711,937 filed by Gharib et al. on Feb. 24, 2010 now U.S. Pat. No. 7,920,922 (the contents being incorporated herein by reference) which is a continuation of U.S. patent application Ser. No. 10/754,899 filed by Gharib et al. on Jan. 9, 2004 (the contents being incorporated herein by reference), which is a continuation of PCT Patent Application Ser. No. PCT/US02/22247 filed on Jul. 11, 2002 and published as WO03/005887 (the contents being incorporated herein by reference).

BACKGROUND OF THE INVENTION

I. Field of the Invention

This invention relates to nerve monitoring systems and to nerve muscle monitoring systems, and more particularly to systems and methods for determining nerve proximity, nerve direction, and pathology during surgery.

II. Description of Related Art

Systems and methods exist for monitoring nerves and nerve muscles. One such system determines when a needle is approaching a nerve. The system applies a current to the needle to evoke a muscular response. The muscular response is visually monitored, typically as a shake or "twitch." When such a muscular response is observed by the user, the needle is considered to be near the nerve coupled to the responsive muscle. These systems require the user to observe the muscular response (to determine that the needle has approached the nerve). This may be difficult depending on the competing tasks of the user. In addition, when general anesthesia is used during a procedure, muscular response may be suppressed, limiting the ability of a user to detect the response.

While generally effective (although crude) in determining nerve proximity, such existing systems are incapable of determining the direction of the nerve to the needle or instrument passing through tissue or passing by the nerves. This can be disadvantageous in that, while the surgeon may appreciate that a nerve is in the general proximity of the instrument, the inability to determine the direction of the nerve relative to the instrument can lead to guess work by the surgeon in advancing the instrument and thereby raise the specter of inadvertent contact with, and possible damage to, the nerve.

Another nerve-related issue in existing surgical applications involves the use of nerve retractors. A typical nerve retractor serves to pull or otherwise maintain the nerve outside the area of surgery, thereby protecting the nerve from inadvertent damage or contact by the "active" instrumentation used to perform the actual surgery. While generally advantageous in protecting the nerve, it has been observed that such retraction can cause nerve function to become impaired or otherwise pathologic over time due to the retraction. In certain surgical applications, such as spinal surgery, it is not possible to determine if such retraction is hurting or damaging the retracted nerve until after the surgery (generally referred to as a change in "nerve health" or "nerve status"). There are also no known techniques or systems for assessing whether a given procedure is having a beneficial effect on a nerve or nerve root known to be pathologic (that is, impaired or otherwise unhealthy).

Based on the foregoing, a need exists for a better system and method that can determine the proximity of a surgical instrument (including but not limited to a needle, catheter, cannula, probe, or any other device capable of traversing through tissue or passing near nerves or nerve structures) to a nerve or group of nerves during surgery. A need also exists for a system and method for determining the direction of the nerve relative to the surgical instrument. A still further need exists for a manner of monitoring nerve health or status during surgical procedures.

The present invention is directed at eliminating, or at least reducing the effects of, the above-described problems with the prior art, as well as addressing the above-identified needs.

SUMMARY OF THE INVENTION

The present invention includes a system and related methods for determining nerve proximity and nerve direction to surgical instruments employed in accessing a surgical target site, as well as monitoring the status or health (pathology) of a nerve or nerve root during surgical procedures.

According to a broad aspect, the present invention includes a surgical system, comprising a control unit and a surgical instrument. The control unit has at least one of computer programming software, firmware and hardware capable of delivering a stimulation signal, receiving and processing neuromuscular responses due to the stimulation signal, and identifying a relationship between the neuromuscular response and the stimulation signal. The surgical instrument has at least one stimulation electrode electrically coupled to said control unit for transmitting the stimulation signal, wherein said control unit is capable of determining at least one of nerve proximity, nerve direction, and nerve pathology relative to the surgical instrument based on the identified relationship between the neuromuscular response and the stimulation signal.

In a further embodiment of the surgical system of the present invention, the control unit is further equipped to communicate at least one of alpha-numeric and graphical information to a user regarding at least one of nerve proximity, nerve direction, and nerve pathology.

In a further embodiment of the surgical system of the present invention, the surgical instrument may comprise at least one of a device for maintaining contact with a nerve during surgery, a device for accessing a surgical target site, and a device for testing screw placement integrity.

In a further embodiment of the surgical system of the present invention, the surgical instrument comprises a nerve root retractor and wherein the control unit determines nerve pathology based on the identified relationship between the neuromuscular response and the stimulation signal.

In a further embodiment of the surgical system of the present invention, the surgical instrument comprises a dilating instrument and wherein the control unit determines at least one of proximity and direction between a nerve and the instrument based on the identified relationship between the neuromuscular response and the stimulation signal.

In a further embodiment of the surgical system of the present invention, the dilating instrument comprises at least one of a K-wire, an obturator, a dilating cannula, and a working cannula.

In a further embodiment of the surgical system of the present invention, the surgical instrument comprises a screw test probe and wherein the control unit determines the proximity between the screw test probe and an exiting spinal nerve root to assess whether a medial wall of a pedicle has been breached by at least one of hole formation and screw placement.

BRIEF DESCRIPTION OF THE DRAWINGS

FIG. 16 is a graph illustrating a simulated recruitment curve generated by a "virtual patient" device and method according to the present invention.

DESCRIPTION OF THE SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
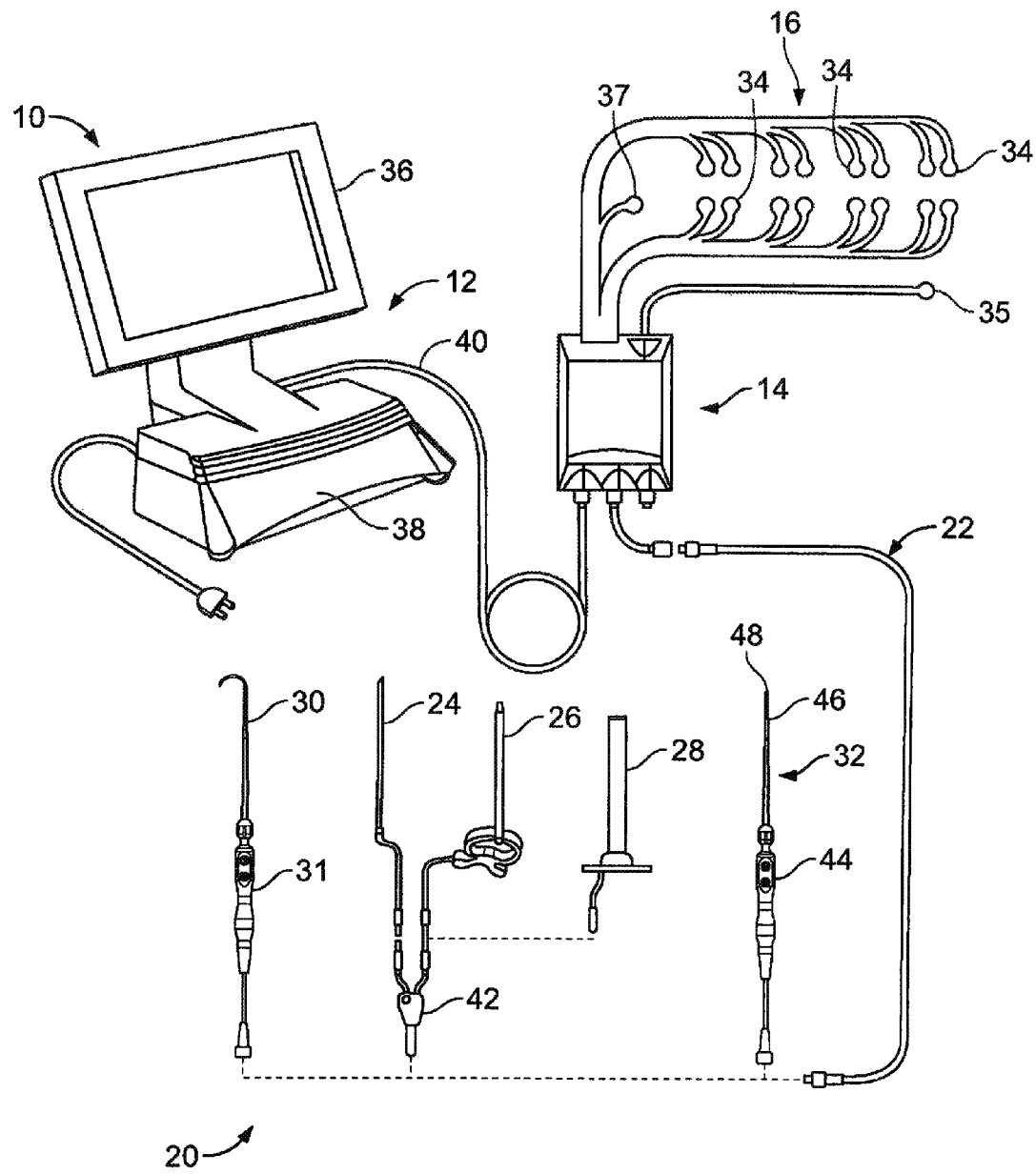
FIG. 1 is a perspective view of a surgical system 10 capable of determining, among other things, nerve proximity, direction, and pathology according to one aspect of the present invention.

FIG. 1 illustrates, by way of example only, a surgical system 10 capable of employing the nerve proximity, nerve direction, and nerve pathology assessments according to the present invention. As will be explained in greater detail below, the surgical system 10 is capable of providing safe and reproducible access to any number of surgical target sites, and well as monitoring changes in nerve pathology (health or status) during surgical procedures. It is expressly noted that, although described herein largely in terms of use in spinal surgery, the surgical system 10 and related methods of the present invention are suitable for use in any number of additional surgical procedures wherein tissue having significant neural structures must be passed through (or near) in order to establish an operative corridor, or where neural structures are retracted.

Figure 2:
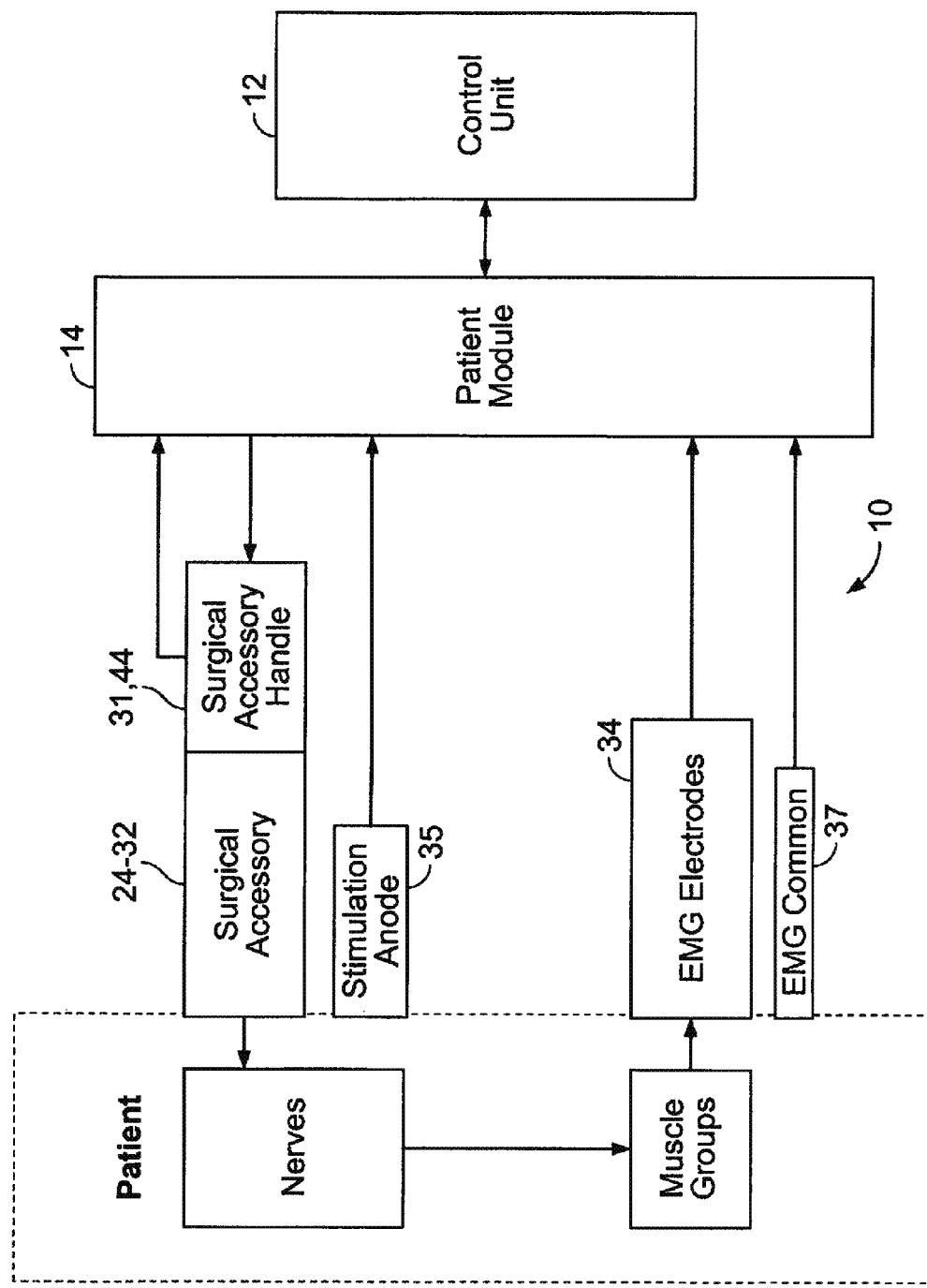
FIG. 2 is a block diagram of the surgical system 10 shown in FIG. 1.

The surgical system 10 includes a control unit 12, a patient module 14, an EMG harness 16 and return electrode 18 coupled to the patient module 14, and a host of surgical accessories 20 capable of being coupled to the patient module 14 via one or more accessory cables 22. The surgical accessories 20 may include, but are not necessarily limited to, surgical access components (such as a K-wire 24, one or more dilating cannula 26, and a working cannula 28), neural pathology monitoring devices (such as nerve root retractor 30), and devices for performing pedicle screw test (such as screw test probe 32). A block diagram of the surgical system 10 is shown in FIG. 2, the operation of which is readily apparent in view of the following description.

The control unit 12 includes a touch screen display 36 and a base 38. The touch screen display 36 is preferably equipped with a graphical user interface (GUI) capable of communicating information to the user and receiving instructions from the user. The base 38 contains computer hardware and software that commands the stimulation sources, receives digitized signals and other information from the patient module 14, and processes the EMG responses to extract characteristic information for each muscle group, and displays the processed data to the operator via the display 36. The primary functions of the software within the control unit 12 include receiving user commands via the touch screen display 36, activating stimulation in the requested mode (nerve proximity, nerve detection, nerve pathology, screw test), processing signal data according to defined algorithms (described below), displaying received parameters and processed data, and monitoring system status and report fault conditions.

The patient module 14 is connected via a serial cable 40 to the control unit 12, and contains the electrical connections to all electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 36 is directed towards the surgeon for easy visualization. The patient module 14 should be located between the patient's legs, or may be affixed to the end of the operating table at mid-leg level using a bedrail clamp. The position selected should be such that the EMG leads can reach their farthest desired location without tension during the surgical procedure.

In a significant aspect of the present invention, the information displayed to the user on display 36 may include, but is not necessarily limited to, alpha-numeric and/or graphical information regarding nerve proximity, nerve direction, nerve pathology, stimulation level, myotome/EMG levels, screw testing, advance or hold instructions, and the instrument in use. In one embodiment (set forth by way of example only) the display includes the following components as set forth in Table 1:

TABLE 1

| Screen Component | Description |
| --- | --- |
| Menu/Status Bar | The mode label may include the surgical accessory attached, such as the surgical access components (K-Wire, Dilating Cannula, Working Cannula), nerve pathology monitoring device (Nerve Root Retractor), and/or screw test device (Screw Test Probe) depending on which is attached. |
| Spine Image | An image of a human body/skeleton showing the electrode placement on the body, with labeled channel number tabs on each side (1-4 on left and right). Left and Right labels will show the patient orientation. The Channel number tabs may be highlighted or colored depending on the specific function being performed. |
| Display Area | Shows procedure-specific information. |
| Myotome & Level Names | A label to indicate the Myotome name and corresponding Spinal Level(s) associated with the channel of interest. |
| Advance/Hold | When in the Detection mode, an indication of "Advance" will show when it is safe to move the cannula forward (such as when the minimum stimulation current threshold $I_{Thresh}$ (described below) is greater than a predetermined value, indicating a safe distance to the nerve) and "Hold" will show when it is unsafe to advance the cannula (such as when the minimum stimulation current threshold $I_{Thresh}$ (described below) is less than a predetermined value, indicating that the nerve is relatively close to the cannula) and during proximity calculations. |
| Function | Indicates which function is currently active (Direction, Detection, Pathology Monitoring, Screw Test). |
| Dilator In Use | A colored circle to indicate the inner diameter of the cannula, with the numeric size. If cannula is detached, no indicator is displayed. |

TABLE 2

| Color | Channel ID | Myotome | Nerve | Spinal Level |
| --- | --- | --- | --- | --- |
| Red | Right 1 | Right Vastus Medialis | Femoral | L2, L3, L4 |
| Orange | Right 2 | Right TibialisAnterior | Peroneal | L4, L5 |
| Yellow | Right 3 | Right Biceps Femoris | Sciatic | L5, S1, S2 |
| Green | Right 4 | Right Gastroc. Medial | Post Tibialis | S1, S2 |
| Blue | Left 1 | Left Vastus Medialis | Femoral | L2, L3, L4 |
| Violet | Left 2 | Left Tibialis Anterior | Peroneal | L4, L5 |
| Gray | Left 3 | Left Biceps Femoris | Sciatic | L5, S1, S2 |
| White | Left 4 | Left Gastroc. Medial | Post Tibialis | S1, S2 |

Although not shown, it will be appreciated that any of a variety of electrodes can be employed, including but not limited to needle electrodes. The EMG responses provide a quantitative measure of the nerve depolarization caused by the electrical stimulus. Analysis of the EMG responses is then used to determine the proximity and direction of the nerve to the stimulation electrode, as will be described with particularity below.

The surgical system 10 accomplishes safe and reproducible access to a surgical target site by detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. The surgical system 10 does so by electrically stimulating nerves via one or more stimulation electrodes at the distal end of the surgical access components 24-28 while monitoring the EMG responses of the muscle groups innervated by the nerves. In a preferred embodiment, this is accomplished via 8 pairs of EMG electrodes 34 placed on the skin over the major muscle groups on the legs (four per side), an anode electrode 35 providing a return path for the stimulation current, and a common electrode 37 providing a ground reference to pre-amplifiers in the patient module 14. By way of example, the placement of EMG electrodes 34 may be undertaken according to the manner shown in Table 2 below for spinal surgery:

The surgical access components 24-28 are designed to bluntly dissect the tissue between the patient's skin and the surgical target site. An initial dilating cannula 26 is advanced towards the target site, preferably after having been aligned using any number of commercially available surgical guide frames. An obturator (not shown) may be included inside the initial dilator 26 and may similarly be equipped with one or more stimulating electrodes. Once the proper location is achieved, the obturator (not shown) may be removed and the K-wire 24 inserted down the center of the initial dilating cannula 26 and docked to the given surgical target site, such as the annulus of an intervertebral disc. Cannulae of increasing diameter are then guided over the previously installed cannula 26 until the desired lumen is installed. By way of example only, the dilating cannulae 26 may range in diameter from 6 mm to 30 mm. In one embodiment, each cannula 26 has four orthogonal stimulating electrodes at the tip to allow detection and direction evaluation, as will be described below.

The working cannula 28 is installed over the last dilating cannula 26 and then all the dilating cannulae 26 are removed from inside the inner lumen of the working cannula 28 to establish the operative corridor therethrough. A stimulator driver 42 is provided to electrically couple the particular surgical access component 24-28 to the patient module 14 (via accessory cable 22). In a preferred embodiment, the stimulator driver 42 includes one or more buttons for selectively activating the stimulation current and/or directing it to a particular surgical access component.

The surgical system 10 accomplishes neural pathology monitoring by electrically stimulating a retracted nerve root via one or more stimulation electrodes at the distal end of the nerve root retractor 30 while monitoring the EMG responses of the muscle group innervated by the particular nerve. The EMG responses provide a quantitative measure of the nerve depolarization caused by the electrical stimulus. Analysis of the EMG responses may then be used to assess the degree to which retraction of a nerve or neural structure affects the nerve function over time, as will be described with greater particularity below. One advantage of such monitoring, by way of example only, is that the conduction of the nerve may be monitored during the procedure to determine whether the neurophysiology and/or function of the nerve changes (for the better or worse) as the result of the particular surgical procedure. For example, it may be observed that the nerve conduction increases as the result of the operation, indicating that the previously inhibited nerve has been positively affected by the operation. The nerve root retractor 30 may comprise any number of suitable devices capable of maintaining contact with a nerve or nerve root. The nerve root retractor 30 may be dimensioned in any number of different fashions, including having a generally curved distal region (shown as a side view in FIG. 1 to illustrate the concave region where the nerve will be positioned while retracted), and of sufficient dimension (width and/or length) and rigidity to maintain the retracted nerve in a desired position during surgery. The nerve root retractor 30 may also be equipped with a handle 31 having one or more buttons for selectively applying the electrical stimulation to the stimulation electrode(s) at the end of the nerve root retractor 30. In one embodiment, the nerve root retractor 30 is disposable and the handle 31 is reusable and autoclavable.

The surgical system 10 can also be employed to perform screw test assessments via the use of screw test probe 32. The screw test probe 32 is used to test the integrity of pedicle holes (after formation) and/or screws (after introduction). The screw test probe 32 includes a handle 44 and a probe member 46 having a generally ball-tipped end 48. The handle 44 may be equipped with one or more buttons for selectively applying the electrical stimulation to the ball-tipped end 48 at the end of the probe member 46. The ball tip 48 of the screw test probe 32 is placed in the screw hole prior to screw insertion or placed on the installed screw head. If the pedicle wall has been breached by the screw or tap, the stimulation current will pass through to the adjacent nerve roots and they will depolarize at a lower stimulation current.

Upon pressing the button on the screw test handle 44, the software will execute an algorithm that results in all channel tabs being color-coded to indicate the detection status of the corresponding nerve. The channel with the "worst" (lowest) level will be highlighted (enlarged) and that myotome name will be displayed, as well as graphically depicted on the spine diagram. A vertical bar chart will also be shown, to depict the stimulation current required for nerve depolarization in mA for the selected channel. The screw test algorithm preferably determines the depolarization (threshold) current for all 8 EMG channels. The surgeon may also set a baseline threshold current by stimulating a nerve root directly with the screw test probe 32. The surgeon may choose to display the screw test threshold current relative to this baseline. The handle 44 may be equipped with a mechanism (via hardware and/or software) to identify itself to the system when it is attached. In one embodiment, the probe member 46 is disposable and the handle 44 is reusable and autoclavable.

An audio pick-up (not shown) may also be provided as an optional feature according to the present invention. In some cases, when a nerve is stretched or compressed, it will emit a burst or train of spontaneous nerve activity. The audio pick-up is capable of transmitting sounds representative of such activity such that the surgeon can monitor this response on audio to help him determine if there has been stress to the nerve.

Figure 3:
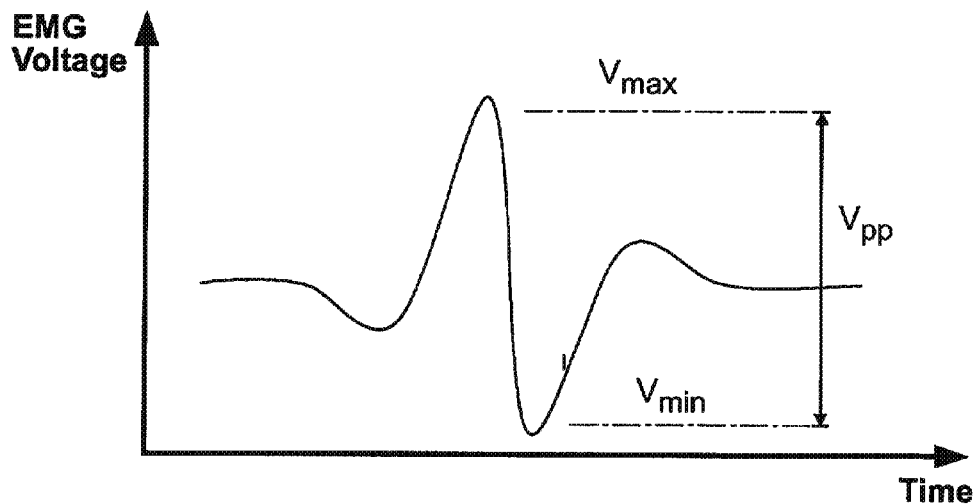
FIG. 3 is a graph illustrating a plot of the neuromuscular response (EMG) of a given myotome over time based on a current stimulation pulse (similar to that shown in FIG. 4) applied to a nerve bundle coupled to the given myotome.
Figure 4:
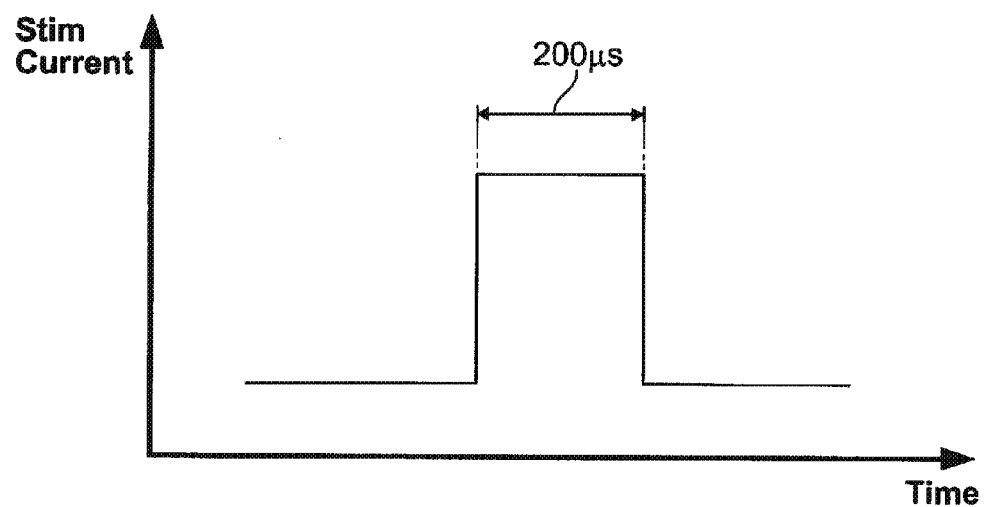
FIG. 4 is a graph illustrating a plot of a stimulation current pulse capable of producing a neuromuscular response (EMG) of the type shown in FIG. 3.

Analysis of the EMG responses according to the present invention will now be described. The nerve proximity, nerve direction, and nerve pathology features of the present invention are based on assessing the evoked response of the various muscle myotomes monitored by the surgical system 10. This is best shown in FIGS. 3-4, wherein FIG. 3 illustrates the evoked response (EMG) of a monitored myotome to the stimulation current pulse shown in FIG. 4. The EMG response can be characterized by a peak to peak voltage of $V_{pp}=V_{max}-V_{min}$. The stimulation current is preferably DC coupled and comprised of monophasic pulses of 200 microsecond duration with frequency and amplitude that is adjusted by the software. For each nerve and myotome there is a characteristic delay from the stimulation current pulse to the EMG response.

Figure 5:
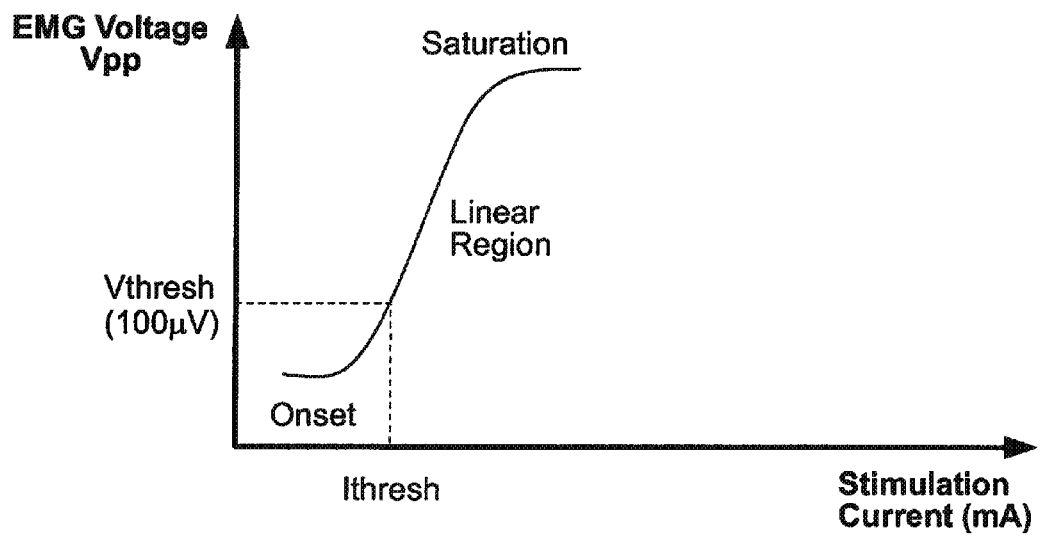
FIG. 5 is a graph illustrating a plot of peak-to-peak voltage (Vpp) for each given stimulation current level ($I_{Stim}$) forming a stimulation current pulse train according to the present invention (otherwise known as a "recruitment curve")

As shown in FIG. 5, there is a threshold stimulation current required to depolarize the main nerve trunk. Below this threshold, current stimulation does not evoke a significant $V_{pp}$ response. Once the stimulation threshold is reached, the evoked response is reproducible and increases with increasing stimulation, as shown in FIG. 5. This is known as a "recruitment curve." In one embodiment, a significant Vpp is defined to be a minimum of 100 uV. The lowest stimulation current that evoked this threshold voltage is called $I_{thresh}$. $I_{thresh}$ decreases as the stimulation electrode approaches the nerve. This value is useful to surgeons because it provides a relative indication of distance (proximity) from the electrode to the nerve.

Figure 6:
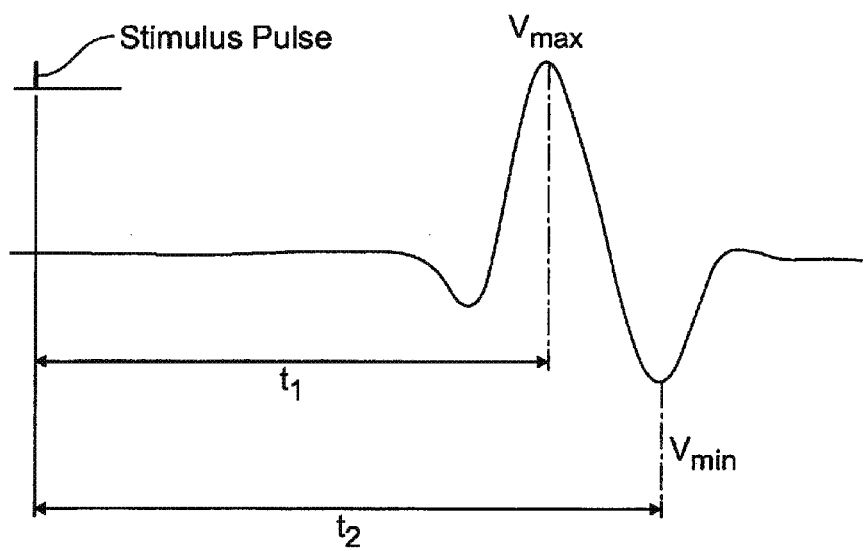
FIG. 6 is a graph illustrating a plot of a neuromuscular response (EMG) over time (in response to a stimulus current pulse) showing the manner in which maximum voltage ($V_{Max}$) and minimum voltage ($V_{Min}$) occur at times T1 and T2, respectively.

As shown in FIG. 6, for each nerve/myotome combination there is a characteristic delay from the stimulation current pulse to the EMG response. For each stimulation current pulse, the time from the current pulse to the first max/min is $T_1$ and to the second max/min is $T_2$. The first phase of the pulse may be positive or negative. As will be described below, the values of $T_1, T_2$ are each compiled into a histogram with bins as wide as the sampling rate. New values of $T_1, T_2$ are acquired with each stimulation and the histograms are continuously updated. The value of $T_1$ and $T_2$ used is the center value of the largest bin in the histogram. The values of $T_1, T_2$ are continuously updated as the histograms change. Initially Vpp is acquired using a window that contains the entire EMG response. After 20 samples, the use of $T_1, T_2$ windows is phased in over a period of 200 samples. Vmax and Vmin are then acquired only during windows centered around $T_1, T_2$ with widths of, by way of example only, 5 msec. This method of acquiring $V_{pp}$ is advantageous in that it automatically performs artifact rejection (as will be described in greater detail below).

As will be explained in greater detail below, the use of the "recruitment curve" according to the present invention is advantageous in that it provides a great amount of useful data from which to make various assessments (including, but not limited to, nerve detection, nerve direction, and nerve pathology monitoring). Moreover, it provides the ability to present simplified yet meaningful data to the user, as opposed to the actual EMG waveforms that are displayed to the users in traditional EMG systems. Due to the complexity in interpreting EMG waveforms, such prior art systems typically require an additional person specifically trained in such matters. This, in turn, can be disadvantageous in that it translates into extra expense (having yet another highly trained person in attendance) and oftentimes presents scheduling challenges because most hospitals do not retain such personnel. To account for the possibility that certain individuals will want to see the actual EMG waveforms, the surgical system 10 includes an Evoked Potentials display that shows the voltage waveform for all 8 EMG channels in real time. It shows the response of each monitored myotome to a current stimulation pulse. The display is updated each time there is a stimulation pulse. The Evoked Potentials display may be accessed during Detection, Direction, or Nerve Pathology Monitoring.

Nerve Detection (Proximity)

The Nerve Detection function of the present invention is used to detect a nerve with a stimulation electrode (i.e. those found on the surgical access components 24-28) and to give the user a relative indication of the proximity of the nerve to the electrode are advanced toward the surgical target site. A method of nerve proximity detection according one embodiment of the present invention is summarized as follows: (1) stimulation current pulses are emitted from the electrode with a fixed pulse width of 200 μs and a variable amplitude; (2) the EMG response of the associated muscle group is measured; (3) the Vpp of the EMG response is determined using T1, T2, and Fmax (NB: before T2 is determined, a constant Fsafe is used for Fmax); (4) a rapid hunting detection algorithm is used to determine $I_{Thresh}$ for a known Vthresh minimum; (5) the value of $I_t$ is displayed to the user as a relative indication of the proximity of the nerve, wherein the $I_{Thresh}$ is expected to decrease as the probe gets closer to the nerve. A detailed description of the algorithms associated with the foregoing steps will follow after a general description of the manner in which this proximity information is communicated to the user.

The Detection Function displays the value of $I_{thresh}$ to the surgeon along with a color code so that the surgeon may use this information to avoid contact with neural tissues. This is shown generally in FIG. 7, which illustrates an exemplary screen display according to the present invention. Detection display is based on the amplitude of the current ($I_{thresh}$) required to evoke an EMG Vpp response greater than $V_{thresh}$ (nominally 100 uV). According to one embodiment, if $I_{thresh}$ is <=4 mA red is displayed, the absolute value of $I_{thresh}$ is displayed. If 4 mA<$I_{thresh}$<10 mA yellow is displayed. If $I_{thresh}$>=10 mA green is displayed. Normally, $I_{thresh}$ is only displayed when it is in the red range. However, the surgeon has the option of displaying $I_{thresh}$ for all three ranges (red, yellow, green). The maximum stimulation current is preferably set by the user and is preferably within the range of between 0-100 mA. Detection is performed on all 4 channels of the selected side. EMG channels on the opposite side are not used. The first dilator 26 may use an obturator having an electrode for stimulation. In one embodiment, all subsequent dilators 26 and the working cannula 28 use four electrodes for stimulation. The lowest value of $I_{thresh}$ from the 4 electrodes is used for display. There is an "Advance/Hold" display that tells the surgeon when the calculations are finished and he may continue to advance the instrument.

The threshold-hunting algorithm employs a series of monopolar stimulations to determine the stimulation current threshold for each EMG channel that is in scope. The nerve is stimulated using current pulses with amplitude of Istim. The muscle groups respond with an evoked potential that has a peak to peak voltage of Vpp. The object of this algorithm is to quickly find $I_{Thresh}$. This is the minimum Istim that results in a Vpp that is greater than a known threshold voltage Vthresh. The value of Istim is adjusted by a bracketing method as follows. The first bracket is 0.2 mA and 0.3 mA. If the Vpp corresponding to both of these stimulation currents is lower than Vthresh, then the bracket size is doubled to 0.2 mA and 0.4 mA. This exponential doubling of the bracket size continues until the upper end of the bracket results in a Vpp that is above Vthresh. The size of the brackets is then reduced by a bisection method. A current stimulation value at the midpoint of the bracket is used and if this results in a Vpp that is above Vthresh, then the lower half becomes the new bracket. Likewise, if the midpoint Vpp is below Vthresh then the upper half becomes the new bracket. This bisection method is used until the bracket size has been reduced to Ires mA. $I_{Thresh}$ is the value of Istim that is the higher end of the bracket.

More specifically, with reference to FIGS. 8A-8E, the threshold hunting will support three states: bracketing, bisection, and monitoring. A stimulation current bracket is a range of stimulation currents that bracket the stimulation current threshold $I_{Thresh}$. The upper and/or lower boundaries of a bracket may be indeterminate. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method below to select stimulation currents and identify stimulation current brackets for each EMG channel in scope.

The method for finding the minimum stimulation current uses the methods of bracketing and bisection. The "root" is identified for a function that has the value −1 for stimulation currents that do not evoke adequate response; the function has the value +1 for stimulation currents that evoke a response. The root occurs when the function jumps from −1 to +1 as stimulation current is increased: the function never has the value of precisely zero. The root will not be known precisely, but only with some level of accuracy. The root is found by identifying a range that must contain the root. The upper bound of this range is the lowest stimulation current $I_{Thresh}$ where the function returns the value +1, i.e. the minimum stimulation current that evokes response.

Figure 8A:
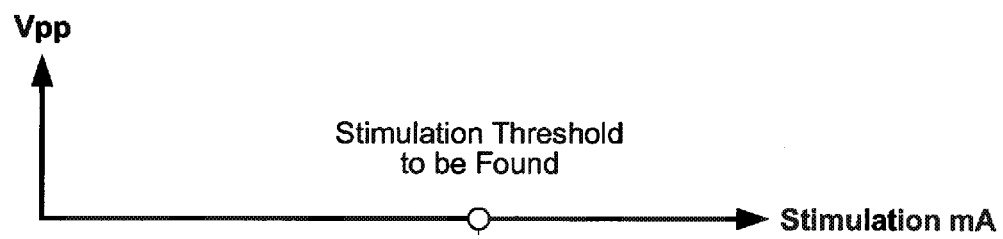
FIGS. 8A-8E are graphs illustrating a rapid current threshold-hunting algorithm according to one embodiment of the present invention.
Figure 8B:
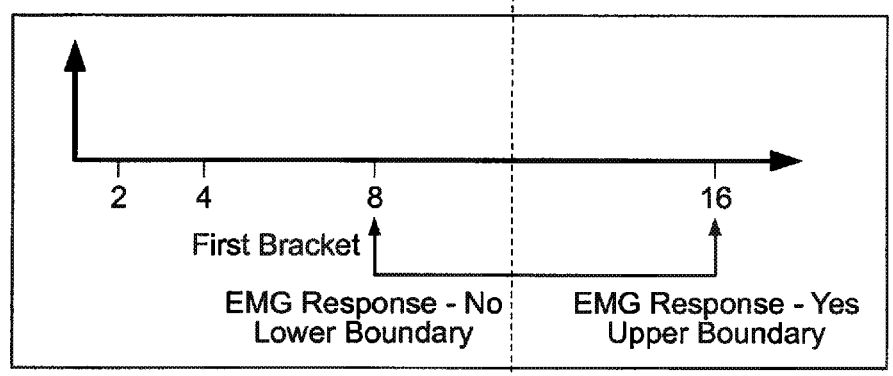
Figure 8C:
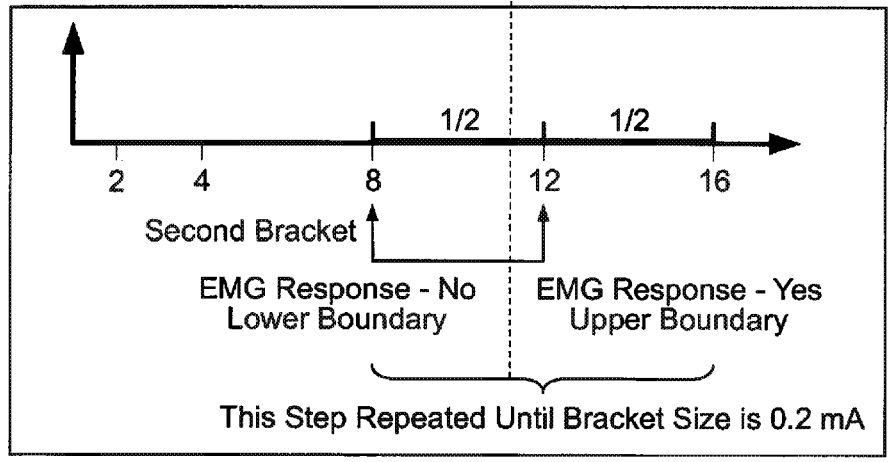
Figure 8A:
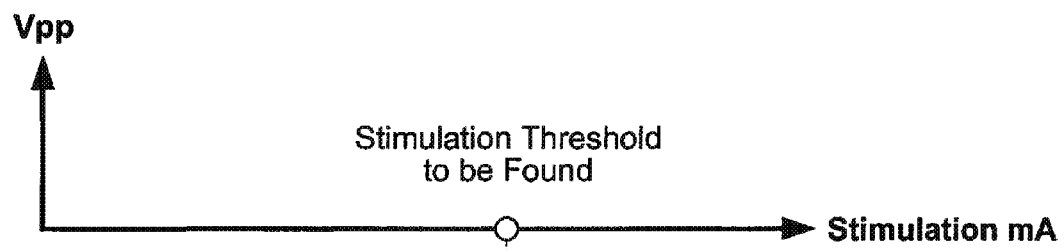
Figure 8D:
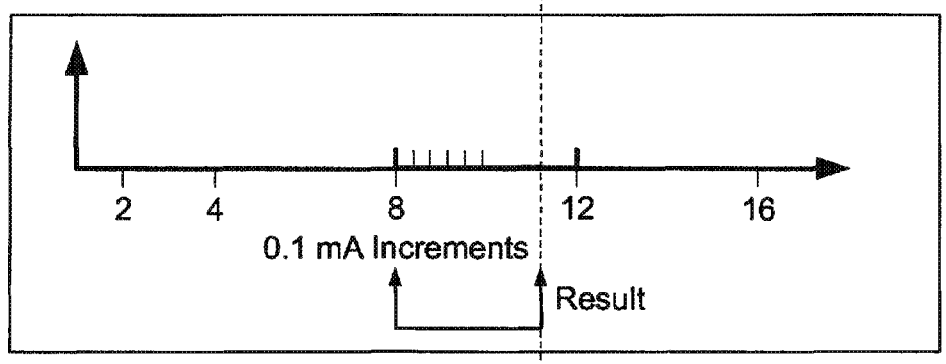
Figure 8E:
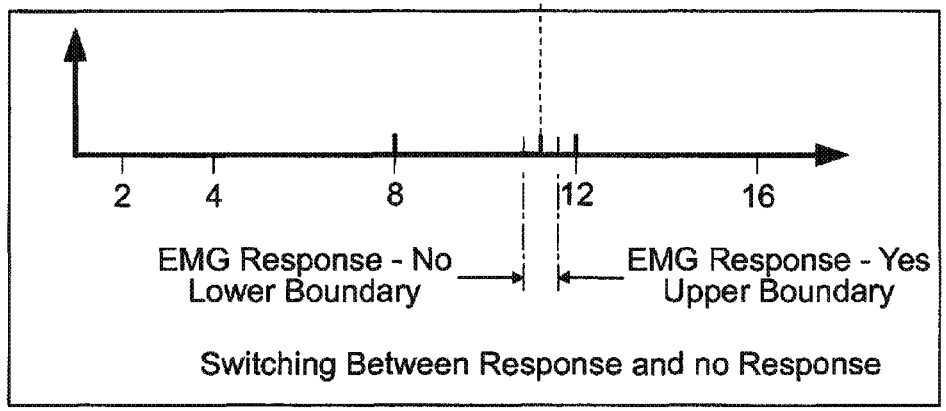

The proximity function begins by adjusting the stimulation current until the root is bracketed (FIG. 8B). The initial bracketing range may be provided in any number of suitable ranges. In one embodiment, the initial bracketing range is 0.2 to 0.3 mA. If the upper stimulation current does not evoke a response, the upper end of the range should be increased. The range scale factor is 2. The stimulation current should never be increased by more than 10 mA in one iteration. The stimulation current should never exceed the programmed maximum stimulation current. For each stimulation, the algorithm will examine the response of each active channel to determine whether it falls within that bracket. Once the stimulation current threshold of each channel has been bracketed, the algorithm transitions to the bisection state.

During the bisection state (FIGS. 8C and 8D), threshold hunting will employ the method described below to select stimulation currents and narrow the bracket to a width of 0.1 mA for each EMG channel with an in-range threshold. After the minimum stimulation current has been bracketed (FIG. 8B), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The proximity algorithm is locked on the electrode position when the response threshold is bracketed by stimulation currents separated by 0.1 mA. The process is repeated for each of the active channels until all thresholds are precisely known. At that time, the algorithm enters the monitoring state.

During the monitoring state (FIG. 8E), threshold hunting will employ the method described below to select stimulation currents and identify whether stimulation current thresholds are changing. In the monitoring state, the stimulation current level is decremented or incremented by 0.1 mA, depending on the response of a specific channel. If the threshold has not changed then the lower end of the bracket should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket.

Figure 9:
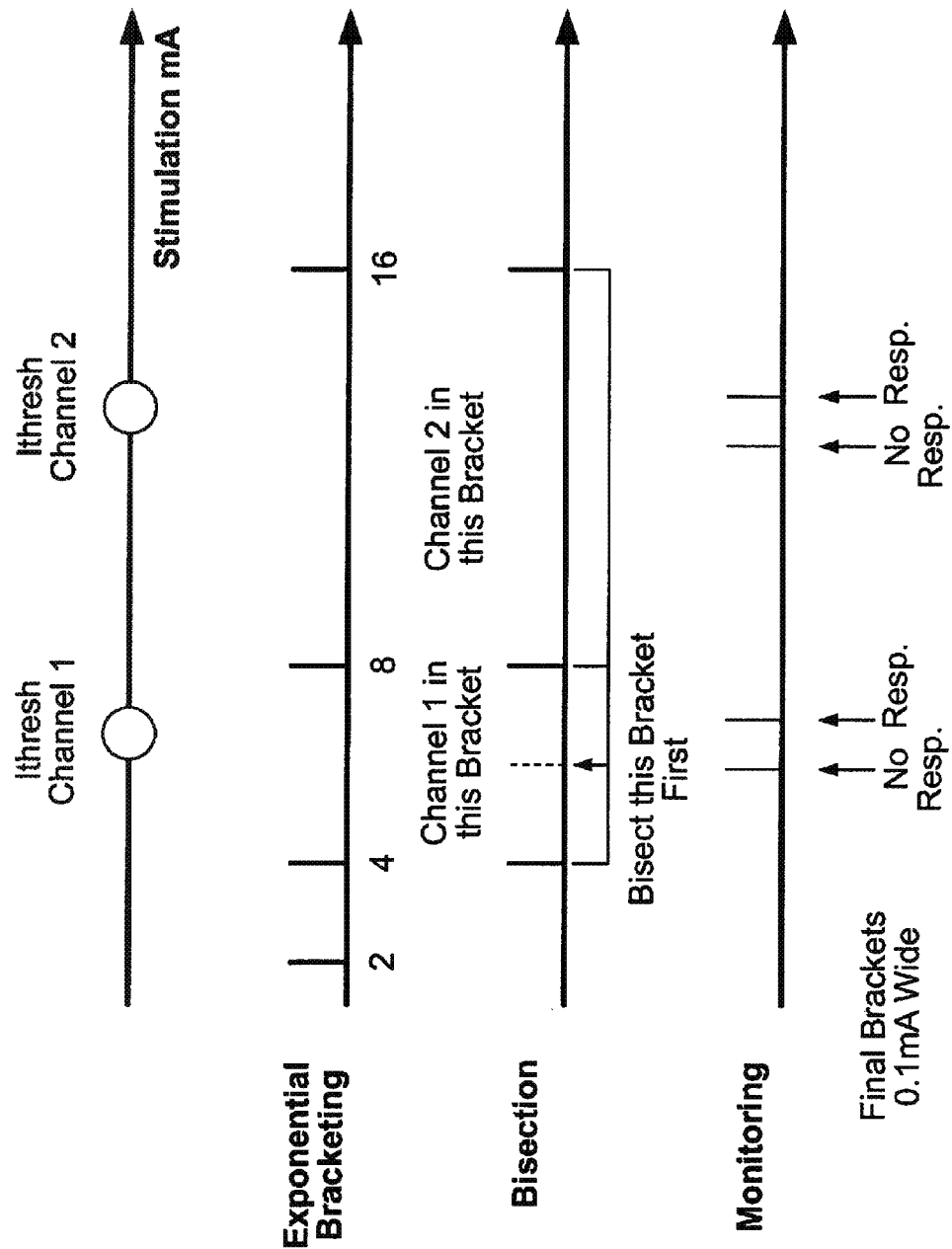
FIG. 9 is a series of graphs illustrating a multi-channel rapid current threshold-hunting algorithm according to one embodiment of the present invention.

When it is necessary to determine the stimulation current thresholds ($I_t$) for more than one channel, they will be obtained by time-multiplexing the threshold-hunting algorithm as shown in FIG. 9. During the bracketing state, the algorithm will start with a stimulation current bracket of 0.2 mA and increase the size of the bracket exponentially. With each bracket, the algorithm will measure the Vpp of all channels to determine which bracket they fall into. After this first pass, the algorithm will know which exponential bracket contains the $I_t$ for each channel. Next, during the bisection state, the algorithm will start with the lowest exponential bracket that contains an $I_t$ and bisect it until $I_t$ is found within 0.1 mA. If there are more than one $I_t$ within an exponential bracket, they will be separated out during the bisection process, and the one with the lowest value will be found first. During the monitoring state, the algorithm will monitor the upper and lower boundaries of the brackets for each $I_t$, starting with the lowest. If the $I_t$ for one or more channels is not found in it's bracket, then the algorithm goes back to the bracketing state to re-establish the bracket for those channels.

The method of performing automatic artifact rejection according to the present invention will now be described. As noted above, acquiring $V_{pp}$ according to the present invention (based on T1, T2 shown in FIG. 6) is advantageous in that, among other reasons, it automatically performs artifact rejection. The nerve is stimulated using a series of current pulses above the stimulation threshold. The muscle groups respond with an evoked potential that has a peak to peak voltage of Vpp. For each EMG response pulse, T1 is the time is measured from the stimulus pulse to the first extremum (Vmax or Vmin) T2 is the time measured from the current pulse to the second extremum (Vmax or Vmin).

The values of T1 and T2 are each compiled into a histogram with Tbin msec bin widths. The value of T1 and T2 used for artifact rejection is the center value of the largest bin in the histogram. To reject artifacts when acquiring the EMG response, Vmax and Vmin are acquired only during windows that are T1±Twin and T2±Twin. Again, with reference to FIG. 6, Vpp is Vmax−Vmin.

Figure 10:
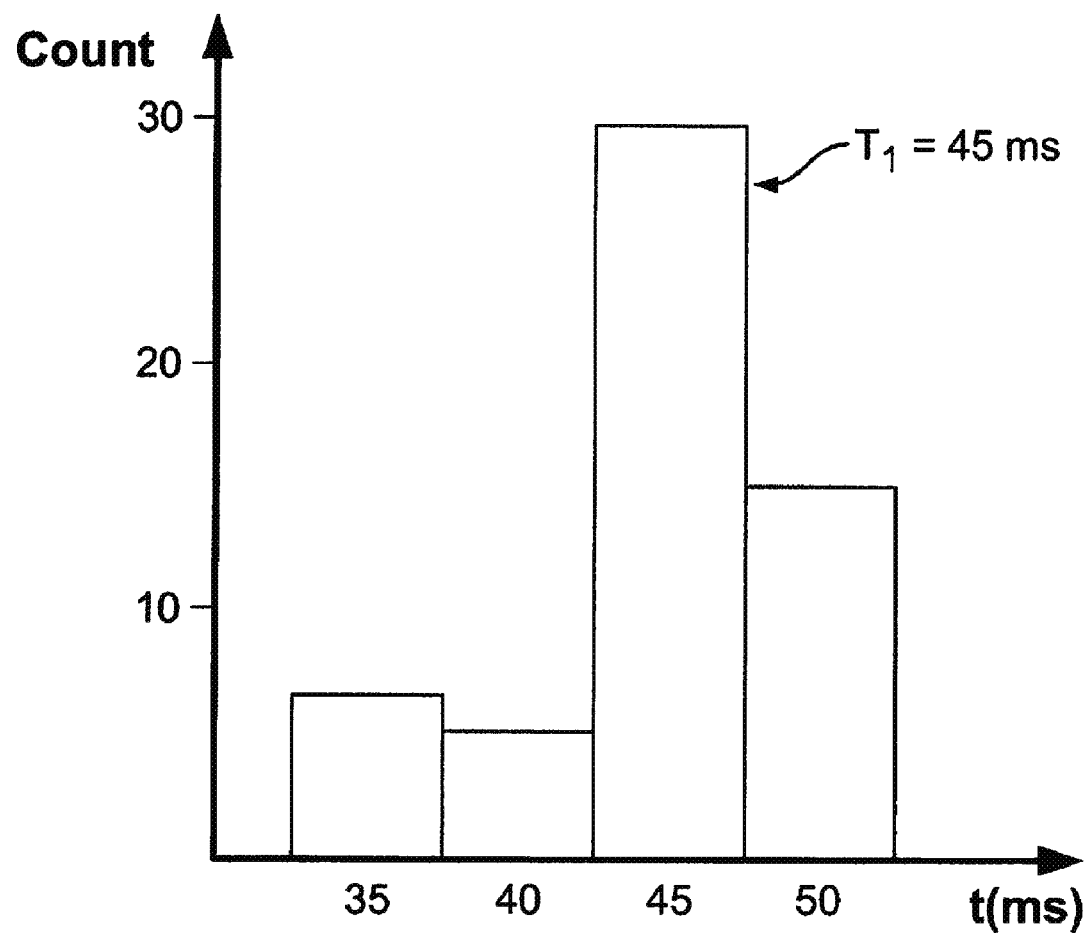
FIG. 10 is a graph illustrating a T1, T2 artifact rejection technique according to one embodiment of the present invention via the use of histograms.
Figure 11:
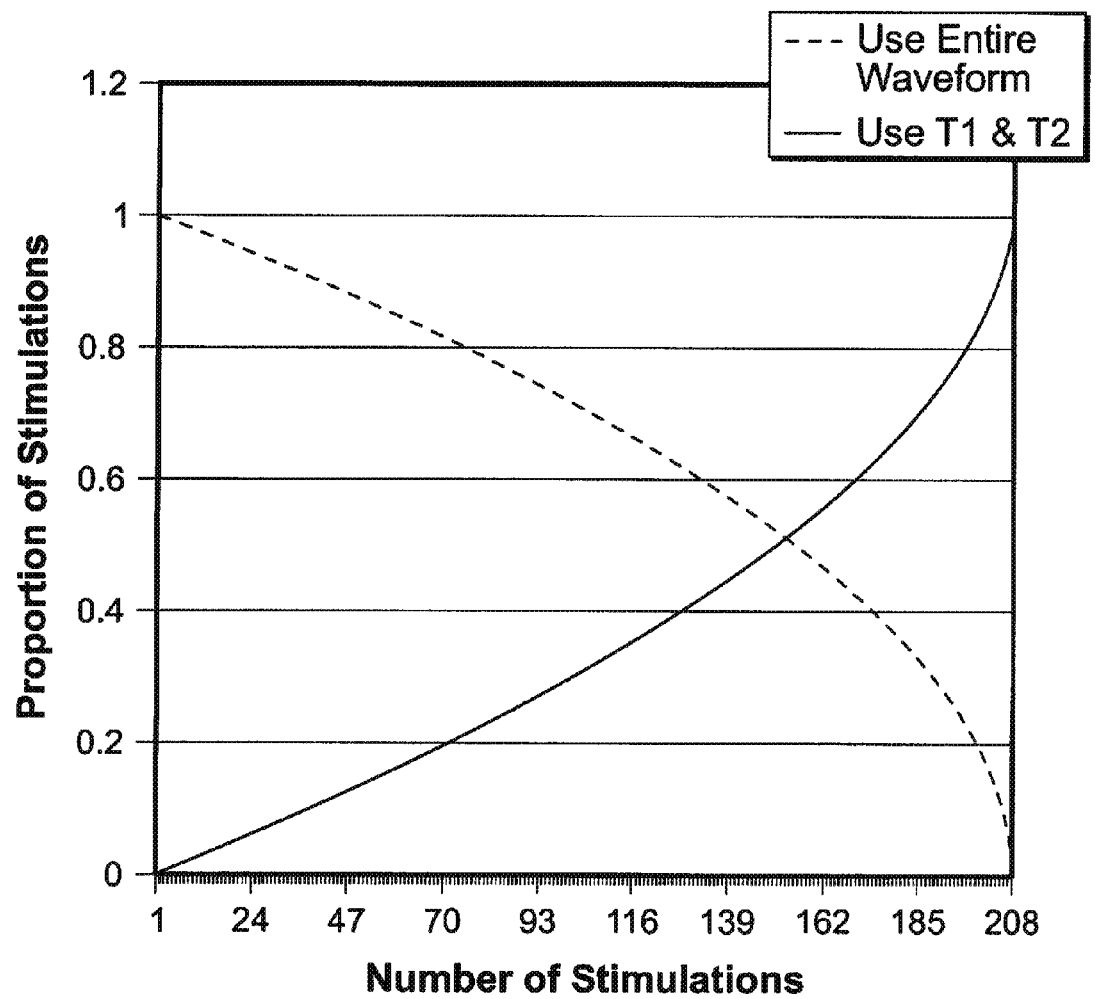
FIG. 11 is a graph illustrating the proportion of stimulations versus the number of stimulations employed in the T1, T2 artifact rejection technique according to the present invention.

The method of automatic artifact rejection is further explained with reference to FIG. 10. While the threshold hunting algorithm is active, after each stimulation, the following steps are undertaken for each EMG sensor channel that is in scope: (1) the time sample values for the waveform maximum and minimum (after stimulus artifact rejection) will be placed into a histogram; (2) the histogram bin size will be the same granularity as the sampling period; (3) the histogram will be emptied each time the threshold hunting algorithm is activated; (4) the histogram will provide two peaks, or modes, defined as the two bins with the largest counts; (5) the first mode is defined as T1; the second mode is defined as T2; (6) a (possibly discontinuous) range of waveform samples will be identified; (7) for the first stimulation after the threshold hunting algorithm is activated, the range of samples will be the entire waveform; (8) after a specified number of stimulations, the range of samples will be limited to T1±0.5 ms and T2±0.5 ms; and (9) before the specified number of stimulations, either range may be used, subject to this restriction: the proportion of stimulations using the entire waveform will decrease from 100% to 0% (a sample of the curve governing this proportion is shown in FIG. 11). Peak-to-peak voltage (Vpp) will be measured either over the identified range of waveform samples. The specified number of stimulations will preferably be between 220 and 240.

Figure 12:
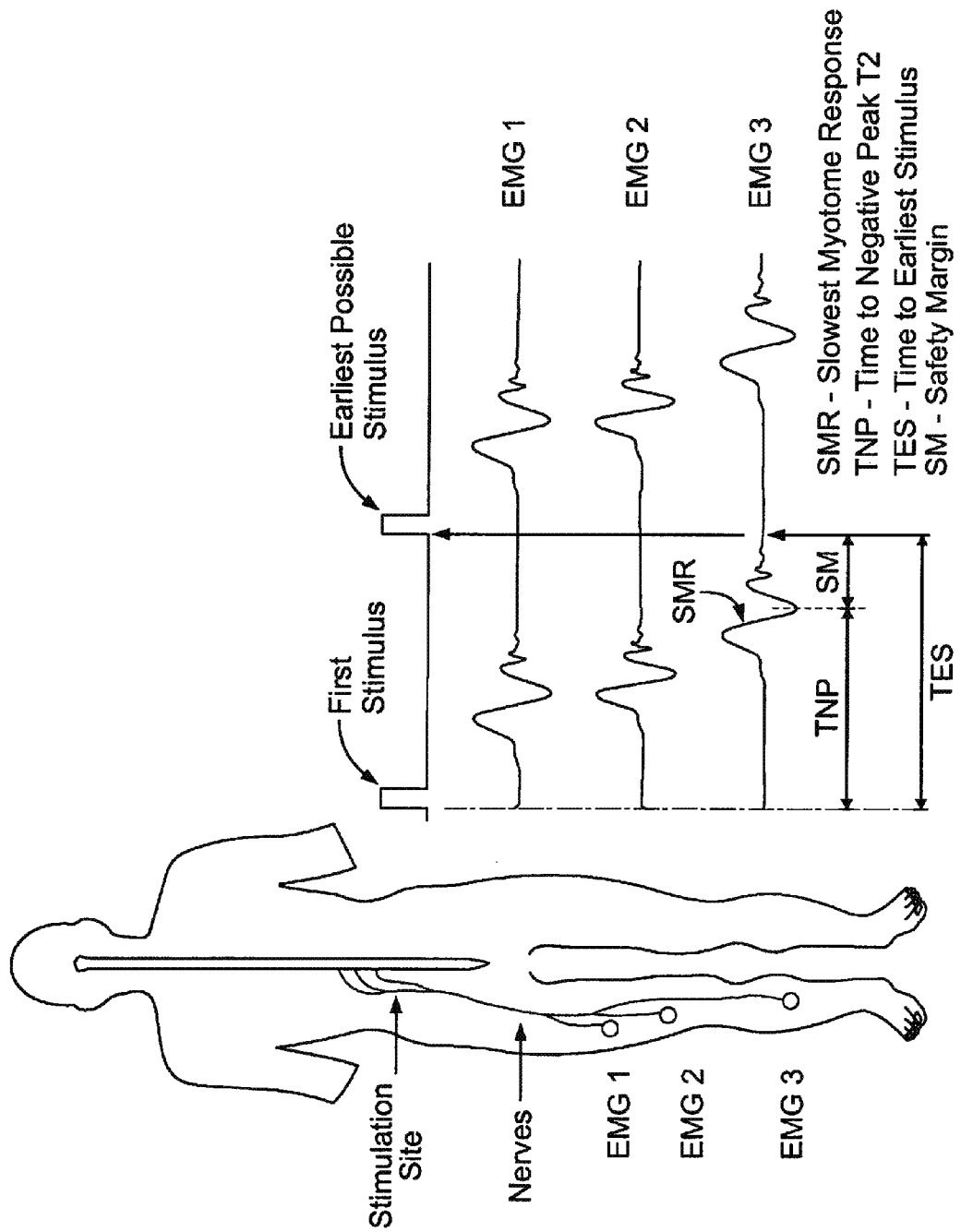
FIG. 12 is an illustrating (graphical and schematic) of a method of automatically determining the maximum frequency ($F_{Max}$) of the stimulation current pulses according to one embodiment of the present invention.

According to another aspect of the present invention, the maximum frequency of the stimulation pulses is automatically obtained with reference to FIG. 12. After each stimulation, Fmax will be computed as: Fmax=1/(T2+Safety Margin) for the largest value of T2 from each of the active EMG channels. In one embodiment, the Safety Margin is 5 ms, although it is contemplated that this could be varied according to any number of suitable durations. Before the specified number of stimulations, the stimulations will be performed at intervals of 100-120 ms during the bracketing state, intervals of 200-240 ms during the bisection state, and intervals of 400-480 ms during the monitoring state. After the specified number of stimulations, the stimulations will be performed at the fastest interval practical (but no faster than Fmax) during the bracketing state, the fastest interval practical (but no faster than Fmax/2) during the bisection state, and the fastest interval practical (but no faster than Fmax/4) during the monitoring state. The maximum frequency used until $F_{max}$ is calculated is preferably 10 Hz, although slower stimulation frequencies may be used during some acquisition algorithms. The value of $F_{max}$ used is periodically updated to ensure that it is still appropriate. This feature is represented graphically, by way of example only, in FIG. 12. For physiological reasons, the maximum frequency for stimulation will be set on a per-patient basis. Readings will be taken from all myotomes and the one with the slowest frequency (highest T2) will be recorded.

Nerve Direction

Figure 7:
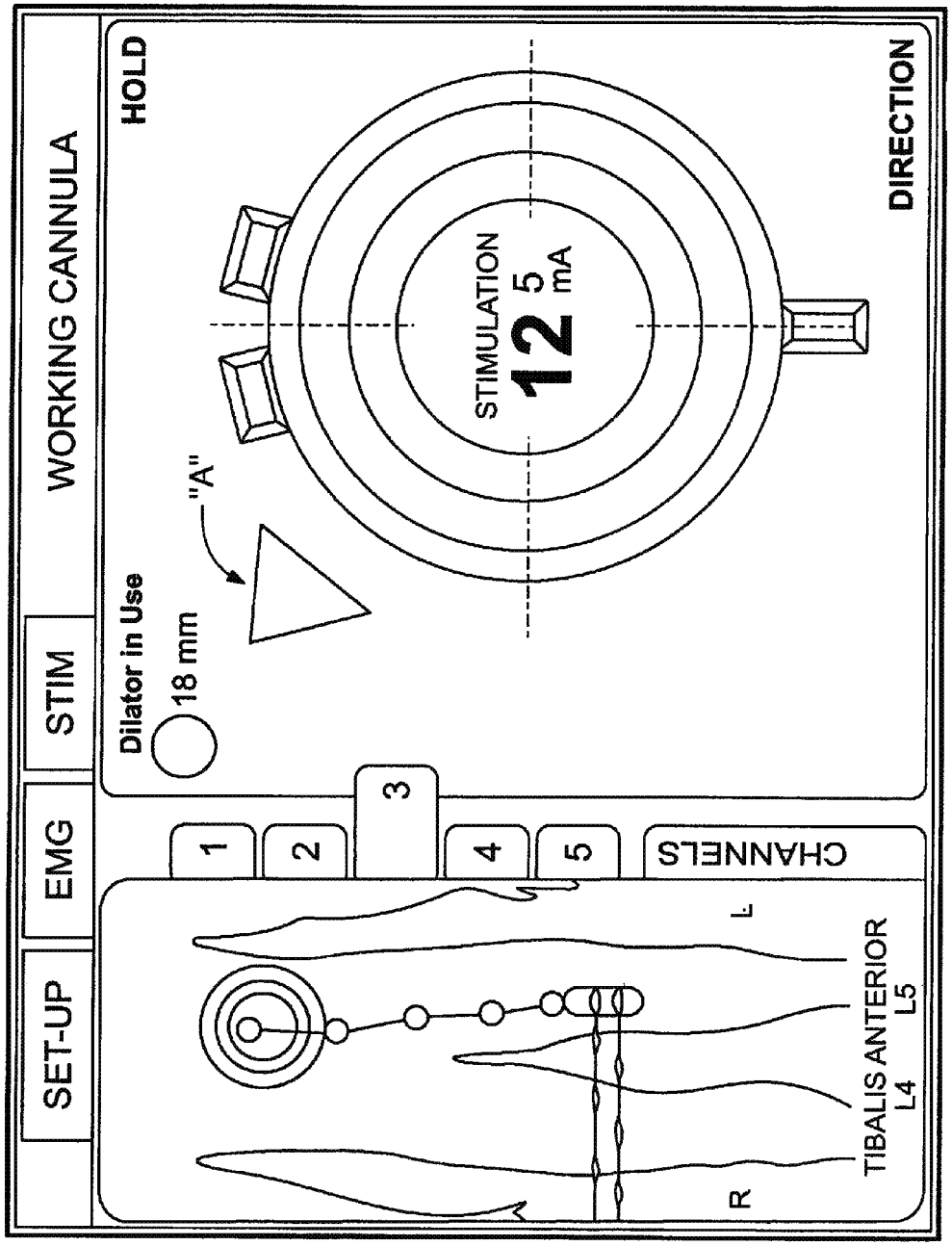
FIG. 7 is an exemplary touch-screen display according to the present invention, capable of communicating a host of alpha-numeric and/or graphical information to a user and receiving information and/or instructions from the user during the operation of the surgical system 10 of FIG. 1.

Once a nerve is detected using the working cannula 28 or dilating cannulae 26, the surgeon may use the Direction Function to determine the angular direction to the nerve relative to a reference mark on the access components 24-28. This is also shown in FIG. 7 as the arrow A pointing to the direction of the nerve. This information helps the surgeon avoid the nerve as he or she advances the cannula. The direction from the cannula to a selected nerve is estimated using the 4 orthogonal electrodes on the tip of the dilating cannula 26 and working cannulae 28. These electrodes are preferably scanned in a monopolar configuration (that is, using each of the 4 electrodes as the stimulation source). The nerve's threshold current ($I_{thresh}$) is found for each of the electrodes by measuring the muscle evoked potential response Vpp and comparing it to a known threshold Vthresh. This algorithm is used to determine the direction from a stimulation electrode to a nerve.

Figure 13:
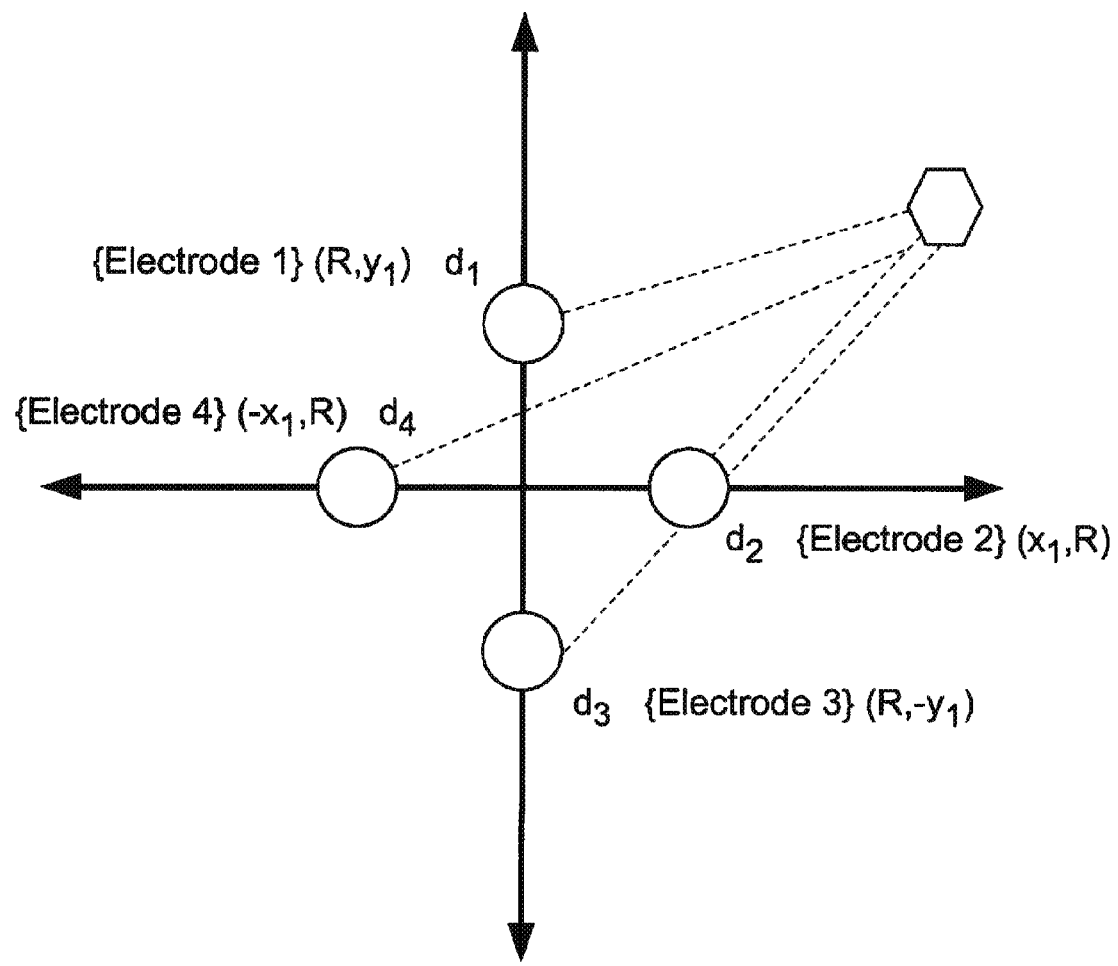
FIG. 13 is a graph illustrating a method of determining the direction of a nerve (denoted as an "octagon") relative to an instrument having four (4) orthogonally disposed stimulation electrodes (denoted by the "circles") according to one embodiment of the present invention.

As shown in FIG. 13, the four (4) electrodes are placed on the x and y axes of a two dimensional coordinate system at radius R from the origin. A vector is drawn from the origin along the axis corresponding to each electrode that has a length equal to $I_{Thresh}$ for that electrode. The vector from the origin to a direction pointing toward the nerve is then computed. This algorithm employs the T1/T2 algorithm discussed above with reference to FIG. 6. Using the geometry shown in FIG. 10, the (x,y) coordinates of the nerve, taken as a single point, can be determined as a function of the distance from the nerve to each of four electrodes. This can be expressly mathematically as follows:

Where the "circles" denote the position of the electrode respective to the origin or center of the cannula and the "octagon" denotes the position of a nerve, and $d_1$, $d_2$, $d_3$, and $d_4$ denote the distance between the nerve and electrodes 1-4 respectively, it can be shown that:

$$x = \frac{d_1^2 - d_3^2}{-4R} \text{ and } y = \frac{d_2^2 - d_4^2}{-4R}$$

Where R is the cannula radius, standardized to 1, since angles and not absolute values are measured.

After conversion from (x,y) to polar coordinates (r,θ), then θ is the angular direction to the nerve. This angular direction is then displayed to the user as shown in FIG. 7, by way of example only, as arrow A pointing towards the nerve. In this fashion, the surgeon can actively avoid the nerve, thereby increasing patient safety while accessing the surgical target site. The surgeon may select any one of the 4 channels available to perform the Direction Function. The surgeon should preferably not move or rotate the instrument while using the Direction Function, but rather should return to the Detection Function to continue advancing the instrument.

Insertion and advancement of the access instruments 24-28 should be performed at a rate sufficiently slow to allow the surgical system 10 to provide real-time indication of the presence of nerves that may lie in the path of the tip. To facilitate this, the threshold current $I_{Thresh}$ may be displayed such that it will indicate when the computation is finished and the data is accurate. For example, when the detection information is up to date and the instrument such that it is now ready to be advanced by the surgeon, it is contemplated to have the color display show up as saturated to communicate this fact to the surgeon. During advancement of the instrument, if a channel's color range changes from green to yellow, advancement should proceed more slowly, with careful observation of the detection level. If the channel color stays yellow or turns green after further advancement, it is a possible indication that the instrument tip has passed, and is moving farther away from the nerve. If after further advancement, however, the channel color turns red, then it is a possible indication that the instrument tip has moved closer to a nerve. At this point the display will show the value of the stimulation current threshold in mA. Further advancement should be attempted only with extreme caution, while observing the threshold values, and only if the clinician deems it safe. If the clinician decides to advance the instrument tip further, an increase in threshold value (e.g. from 3 mA to 4 mA) may indicate the Instrument tip has safely passed the nerve. It may also be an indication that the instrument tip has encountered and is compressing the nerve. The latter may be detected by listening for sporadic outbursts, or "pops", of nerve activity on the free running EMG audio output (as mentioned above). If, upon further advancement of the instrument, the alarm level decreases (e.g., from 4 mA to 3 mA), then it is very likely that the instrument tip is extremely close to the spinal nerve, and to avoid neural damage, extreme caution should be exercised during further manipulation of the Instrument. Under such circumstances, the decision to withdraw, reposition, or otherwise maneuver the instrument is at the sole discretion of the clinician based upon available information and experience. Further radiographic imaging may be deemed appropriate to establish the best course of action.

Nerve Pathology

Figure 14:
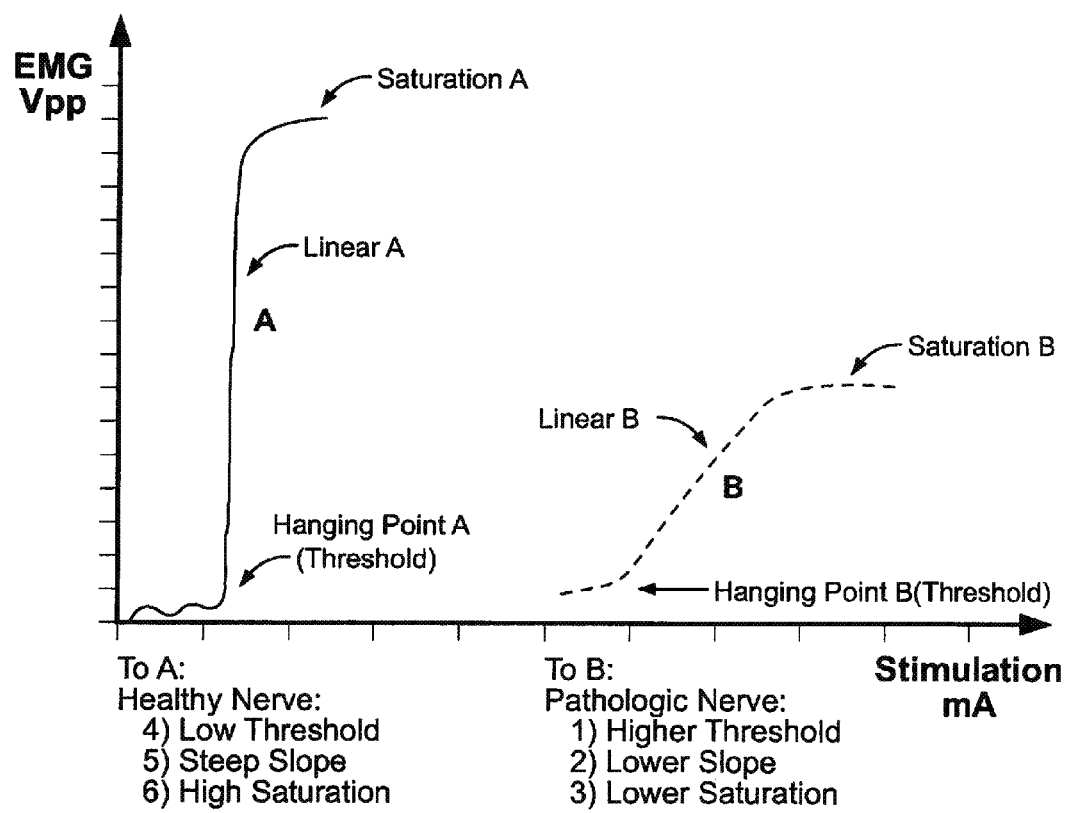
FIG. 14 is a graph illustrating recruitment curves for a generally healthy nerve (denoted "A") and a generally unhealthy nerve (denoted "B") according to the nerve pathology determination method of the present invention.

As noted above, the surgical system 10 accomplishes neural pathology monitoring by electrically stimulating a retracted nerve root via one or more stimulation electrodes at the distal end of the nerve root retractor 30 while monitoring the EMG responses of the muscle group innervated by the particular nerve. FIG. 14 shows the differences between a healthy nerve (A) and a pathologic or unhealthy nerve (B). The inventors have found through experimentation that information regarding nerve pathology (or "health" of "status") can be extracted from the recruitment curves generated according to the present invention (see, e.g., discussion accompanying FIGS. 3-5). In particular, it has been found that a health nerve or nerve bundle will produce a recruitment curve having a generally low threshold or "hanging point" (in terms of both the y-axis or Vpp value and the x-axis or $I_{Stim}$ value), a linear region having a relatively steep slope, and a relatively high saturation region (similar to those shown on recruitment curve "A" in FIG. 14). On the contrary, a nerve or nerve bundle that is unhealthy or whose function is otherwise compromised or impaired (such as being impinged by spinal structures or by prolonged retraction) will produce recruitment curve having a generally higher threshold (again, in terms of both the y-axis or Vpp value and the x-axis or $I_{Stim}$ value), a linear region of reduced slope, and a relatively low saturation region (similar to those shown on recruitment curve "B" in FIG. 14). By recognizing these characteristics, one can monitor nerve root being retracted during a procedure to determine if its pathology or health is affected (i.e. negatively) by such retraction. Moreover, one can monitor a nerve root that has already been deemed pathologic or unhealthy before the procedure (such as may be caused by being impinged by bony structures or a bulging annulus) to determine if its pathology or health is affected (i.e. positively) by the procedure.

The surgical system 10 and related methods have been described above according to one embodiment of the present invention. It will be readily appreciated that various modifications may be undertaken, or certain steps or algorithms omitted or substituted, without departing from the scope of the present invention. By way of example only, certain of these alternate embodiments or methods will be described below.

a. Hanging Point Detection Via Linear Regression

As opposed to identifying the stimulation current threshold ($I_{Thresh}$) based on a predetermined $V_{Thresh}$ (such as described above and shown in FIG. 5), it is also within the scope of the present invention to determine $I_{Thresh}$ via linear regression. This may be accomplished via, by way of example only, the linear regression technique disclosed in commonly owned and co-pending U.S. patent application Ser. No. 09/877,713, filed Jun. 8, 2001 and entitled "Relative Nerve Movement and Status Detection System and Methods," the entire contents of which is hereby expressly incorporated by reference as if set forth in this disclosure in its entirety.

b. Hanging Point Detection Via Dynamic Sweep Subtraction

Figure 15:
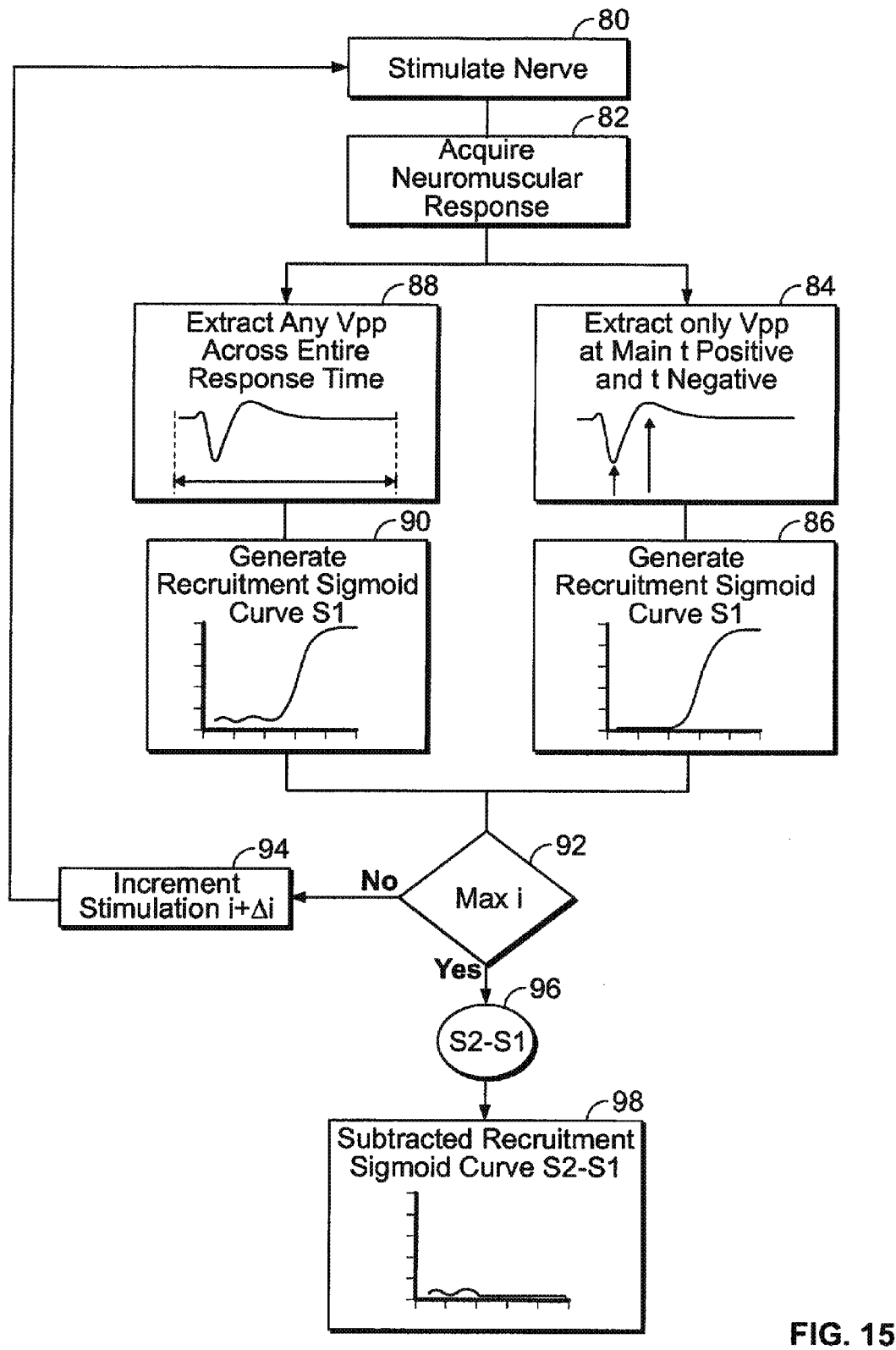
FIG. 15 is flow chart illustrating an alternate method of determining the hanging point of a recruitment curve according to an embodiment of the present invention.

With reference to FIG. 15, the hanging point or threshold may also be determined by the following dynamic sweep subtraction method. The nerve is stimulated in step 80 using current pulses that increase from $I_{Min}$ to $I_{Max}$ (as described above). The resulting the neuromuscular response (evoked EMG) for the associated muscles group is acquired in step 82. The peak-to-peak voltage (Vpp) is then extracted in step 84 for each current pulse according to the T1, T2 algorithm described above with reference to FIGS. 3-6. A first recruitment curve (S1) is then generated by plotting Vpp vs. $I_{Stim}$ in step 86. The same nerve is then stimulated such that, in step 88, the peak-to-peak voltage (Vpp) may be extracted by subtracting the $V_{Max}$ from $V_{Min}$ of each EMG response without the T1, T2 filters employed in step 84. A second recruitment curve (S2) is then generated in step 90 by plotting Vpp vs. $I_{Stim}$. The generation of both recruitment curves S1, S2 continues until the maximum stimulation current ($I_{max}$) is reached (per the decision step 92). If $I_{Max}$ is not reached, the stimulation current $I_{Stim}$ is incremented in step 94. If $I_{max}$ is reached, then the first recruitment curve S1 is subtracted from the second recruitment curve S2 in step 96 to produce the curve "C" shown in step 98. By subtracting S1 from S2, the resulting curve "C" is actually the onset portion of the recruitment curve (that is, the portion before the threshold is reached) for that particular nerve. In this fashion, the last point in the curve "C" is the point with the greatest value of $I_{Stim}$ and hence the hanging point.

c. Peripheral Nerve Pathology Monitoring

Similar to the nerve pathology monitoring scheme described above, the present invention also contemplates the use of one or more electrodes disposed along a portion or portions of an instrument (including, but not limited to, the access components 24-28 described above) for the purpose of monitoring the change, if any, in peripheral nerves during the course of the procedure. In particular, this may be accomplished by disposing one or more stimulation electrodes a certain distance from the distal end of the instrument such that, in use, they will likely come in contact with a peripheral nerve. For example, a mid-shaft stimulation electrode could be used to stimulate a peripheral nerve during the procedure. In any such configuration, a recruitment curve may be generated for the given peripheral nerve such that it can be assessed in the same fashion as described above with regard to the nerve root retractor, providing the same benefits of being able to tell if the contact between the instrument and the nerve is causing pathology degradation or if the procedure itself is helping to restore or improve the health or status of the peripheral nerve.

d. Virtual Patient for Evoked Potential Simulation

With reference to FIG. 16, the present invention also contemplates the use of a "virtual patient" device for simulating a naturally occurring recruitment curve. This is advantageous in that it provides the ability to test the various systems disclosed herein, which one would not be able to test without an animal and/or human subject. Based on the typically high costs of obtaining laboratory and/or surgical time (both in terms of human capital and overhead), eliminating the requirement of performing actual testing to obtain recruitment curves is a significant offering. According to the present invention, this can be accomplished by providing a device (not shown) having suitable software and/or hardware capable of producing the signal shown in FIG. 16. The device will preferably accept a sweeping current signal according to the present invention (that is, 200 microseconds width pulses sweeping in amplitude from 0-100 mA) and produce a voltage pulse having a peak-to-peak voltage (Vpp) that varies with the amplitude of the current input pulse. The relationship of the output Vpp and the input stimulation current will produce a recruitment curve similar to that shown. In one embodiment, the device includes various adjustments such that the features of the recruitment curve may be selectively modified. For example, the features capable of being modified may include, but are not necessarily limited to, Vpp at onset, maximum stimulation current of onselt (hanging point), the slope of the linear region and/or the Vpp of the saturation region.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the scope of the appended claims.

What is claimed is:

1. A method of establishing an operative corridor for spinal surgery, comprising:

mounting a plurality of sensors proximate to selected leg muscles;

activating a nerve monitoring system that outputs a stimulation signal to one or more surgical access instruments and that, in response to signals from the sensors, displays neuromuscular response information which is indicative of nerve proximity;

advancing an initial dilating assembly through bodily tissue having neural structures in a selected path toward a targeted intervertebral disc of a spine, the initial dilating assembly comprising an initial dilator cannula and a removable inner element having at least one stimulation electrode that delivers the stimulation signal to the bodily tissue prior to accessing the spine;

during advancement of the initial dilating assembly through the bodily tissue and prior to accessing the spine, viewing the neuromuscular response information on a display device of the nerve monitoring system when the stimulation signal is delivered to the bodily tissue prior to accessing the spine;

inserting a guide wire through a lumen of the initial dilator cannula after the initial dilator cannula is advanced through the bodily tissue so that the guide wire penetrates an annulus of the targeted intervertebral disc of the spine;

advancing a plurality of sequential dilator cannulas along the selected path toward the targeted intervertebral disc of the spine after the guide wire engages the annulus of the disc;

advancing a working corridor instrument over an outermost dilator cannula of the plurality of sequential dilator cannulas toward the targeted intervertebral disc of the spine after; and establishing an operative corridor to the targeted intervertebral disc of the spine using the working corridor instrument.

2. The method of claim 1, wherein the removable inner element of the initial dilating assembly comprises an obturator arranged inside the initial dilator cannula and the at least one stimulation electrode.

3. The method of claim 1, further comprising removing the removable inner element from the initial dilator cannula prior to inserting the guide wire through the initial dilator cannula.

4. The method of claim 3, further comprising operating one or more buttons of a stimulator driver coupled to the removable inner element of the initial dilating assembly to selectively deliver the stimulation signal.

5. The method of claim 1, further comprising inputting a setting for the stimulation signal using a graphical user interface of the nerve monitoring system.

6. The method of claim 1, wherein the neuromuscular response information is a stimulation current threshold required to evoke a neuromuscular response of greater than or equal to a predetermined magnitude.

7. The method of claim 6, wherein the nerve monitoring system contemporaneously displays the stimulation current threshold which is indicative of nerve proximity and a spine image indicative of sensor placement.

8. The method of claim 6, wherein the nerve monitoring system executes an algorithm to determine the stimulation threshold that is displayed.

9. The method of claim 1, wherein the sensors are EMG electrodes that detect voltage responses from the selected muscles.

10. The method of claim 9, wherein the nerve monitoring system also displays EMG waveforms.

11. The method of claim 10, wherein the EMG waveforms displayed by the nerve monitoring system comprises the voltage waveforms for eight EMG response channels.

12. The method of claim 1, further comprising removing the initial dilator cannula and the plurality of sequential dilator cannulas from the working corridor instrument prior to establishing the operative corridor to the targeted intervertebral disc of the spine.

13. The method of claim 1, wherein the working corridor instrument comprises a cannula that defines an inner lumen.

14. A method of establishing an operative corridor for spinal surgery, comprising:

mounting a plurality of sensors proximate to selected leg muscles;

activating a nerve monitoring system that outputs a stimulation signal to one or more surgical access instruments and that displays neuromuscular response information in response to signals from the sensors;

advancing an initial dilating cannula through bodily tissue having neural structures in a selected path toward a targeted intervertebral disc of a spine, the initial dilating cannula having at least one stimulation electrode that delivers the stimulation signal to the bodily tissue prior to accessing the spine;

during advancement of the initial dilating cannula through the bodily tissue and prior to accessing the spine, monitoring the neuromuscular response information displayed by the nerve monitoring system when the stimulation signal is delivered to the bodily tissue prior to accessing the spine;

inserting a guide wire through a lumen of the initial dilator cannula after the initial dilator cannula is advanced through the bodily tissue so that the guide wire penetrates an annulus of the targeted intervertebral disc of the spine;

advancing a plurality of sequential dilator cannulas along the selected path toward the targeted intervertebral disc of the spine after the guide wire engages the annulus of the disc;

advancing a working corridor instrument over an outermost dilator cannula of the plurality of sequential dilator cannulas toward the targeted intervertebral disc of the spine; and establishing an operative corridor to the targeted intervertebral disc of the spine using the working corridor instrument.

15. The method of claim 14, wherein the neuromuscular response information displayed by the nerve monitoring system comprises a stimulation threshold which is indicative of nerve proximity.

16. The method of claim 15, wherein the nerve monitoring system contemporaneously displays the stimulation threshold which is indicative of nerve proximity and a spine image indicative of sensor placement.

17. The method of claim 14, wherein the neuromuscular response information displayed by the nerve monitoring system comprises EMG voltage waveforms.

18. The method of claim 14, wherein the initial dilating cannula is advanced through the body tissue together with a removable inner element positioned within the initial dilating cannula.

19. The method of claim 18, wherein the removable inner element is removed from the initial dilating cannula prior to inserting the guide wire through the initial dilating cannula.

20. The method of claim 14, wherein the working corridor instrument comprises a cannula that defines an inner lumen.

21. The method of claim 14, wherein the sensors are EMG electrodes that detect voltage responses from the selected muscles.

22. The method of claim 21, wherein the nerve monitoring system also displays EMG waveforms.

23. The method of claim 22, wherein the EMG waveforms displayed by the nerve monitoring system comprises the voltage waveforms for eight EMG response channels.

24. The method of claim 14, wherein the nerve monitoring system executes an algorithm to determine the stimulation threshold that is displayed.

* * * * *